United States Patent
Bhasin

(10) Patent No.: US 9,422,522 B2
(45) Date of Patent: Aug. 23, 2016

(54) METHOD OF PRODUCING ADIPOCYTES FROM FIBROBLAST CELLS

(75) Inventor: Vishal Bhasin, Bondi Beach (AU)

(73) Assignee: Regenertech Pty Limited, Bondi Beach (AU)

( * ) Notice: Subject to any disclaimer, the term of this patent is extended or adjusted under 35 U.S.C. 154(b) by 621 days.

(21) Appl. No.: 12/866,010

(22) PCT Filed: Feb. 5, 2009

(86) PCT No.: PCT/AU2009/000138
§ 371 (c)(1),
(2), (4) Date: Dec. 22, 2010

(87) PCT Pub. No.: WO2009/097657
PCT Pub. Date: Aug. 13, 2009

(65) Prior Publication Data
US 2011/0111030 A1 May 12, 2011

(30) Foreign Application Priority Data
Feb. 5, 2008 (AU) ................ 2008900534

(51) Int. Cl.
*C12N 5/074* (2010.01)
*C12N 5/078* (2010.01)
*C12N 5/077* (2010.01)
*C12N 5/071* (2010.01)
*A61K 35/12* (2015.01)

(52) U.S. Cl.
CPC ........... *C12N 5/0607* (2013.01); *C12N 5/0634* (2013.01); *C12N 5/0653* (2013.01); *C12N 5/0654* (2013.01); *C12N 5/0655* (2013.01); *C12N 5/0676* (2013.01); *A61K 35/12* (2013.01); *C12N 2500/25* (2013.01); *C12N 2500/36* (2013.01); *C12N 2500/38* (2013.01); *C12N 2500/90* (2013.01); *C12N 2500/92* (2013.01); *C12N 2500/95* (2013.01); *C12N 2501/115* (2013.01); *C12N 2501/119* (2013.01); *C12N 2501/125* (2013.01); *C12N 2501/15* (2013.01); *C12N 2501/155* (2013.01); *C12N 2501/22* (2013.01); *C12N 2501/23* (2013.01); *C12N 2501/25* (2013.01); *C12N 2501/385* (2013.01); *C12N 2501/405* (2013.01); *C12N 2501/41* (2013.01); *C12N 2501/70* (2013.01); *C12N 2506/1307* (2013.01); *C12N 2506/1392* (2013.01)

(58) Field of Classification Search
CPC C12N 5/0634; C12N 5/0653; C12N 5/0654; C12N 5/0655; C12N 5/0676; C12N 2500/25; C12N 2500/36; C12N 2500/38; C12N 2500/90; C12N 2500/92; C12N 2500/95; C12N 2501/115; C12N 2501/119; C12N 2501/125; C12N 2501/15; C12N 2501/155; C12N 2501/22; C12N 2501/23; C12N 2501/25; C12N 2501/385; C12N 2501/405; C12N 2501/41; C12N 2501/70; C12N 2506/1307; C12N 2506/1392; A61K 35/12
See application file for complete search history.

(56) References Cited

FOREIGN PATENT DOCUMENTS

| WO | 0162901 | 8/2001 |
|---|---|---|
| WO | 03018780 | 3/2003 |
| WO | 2005054447 | 6/2005 |
| WO | 2005059095 | 6/2005 |
| WO | 2007131200 | 11/2007 |
| WO | 2008116213 | 9/2008 |
| WO | 2009023161 | 2/2009 |

OTHER PUBLICATIONS

Collas et al. Reproductive BioMedicine Online: 762-770, 2006.*
Oliveri et al. Regenerative Medicine, 2(5): 795-816, Sep. 2007.*
Sullivan et al. Reproductive BioMed. Online, 16(1): 41-50, Nov. 2008.*
Broad et al., Eur. J. Biochem, 135: 33-39, 1983.*
Harrison et al., J. of Cell Biology, 100: 429-434, 1985.*
Phelan, from Current Protocols in Cell Biology,1.1.1-1.1.18, Sep. 2007.*
Saito et al., NeuroMolecular Medicine, 7: 79-99, 2005.*
Péault et al., Molecular Therapy, 15(5): 867-877, May 2007.*
Forestell et al., Biotechnology & Bioengineering, 40: 1039-1044, 1992.*
Castaldi, et al. (2007) "Bisperoxovanadium, a Phosphor-Tyrosine Phosphate Inhibitor, Reprograms Myogenic Cells to Acquire a Pluripotent Circulating Phenotype" FASEB J. 21(13):3573-3583.
Rajasingh, et al. (2007) "Abstract 579: De-Differentiation of Somatic Fibroblasts by Mouse Embryonic Stem Cell-Free Extracts: Multi-Lineage Re-Differentiation and Therapeutic Efficacy of Re-Programmed Cells in Mouse Models of Hind Limb and Acute Myocardial Ischemia" Circulation 116(16):Suppl S:105.
Takahashi, et al. (2007) "Induction of Pluripotent Stem Cells from Adult Human Fibroblasts by Defined Factors" Cell 131(5):861-872.
Obokata et al. (2014) "Stimulus-triggered fate conversion of somatic cells into pluripotency" Nature 505:641-7.
Aoi et al (2008) "Generation of Pluripotent Stem Cells from Adult Mouse Liver and Stomach Cells" Science 321:699-702.
Barbuti (2010) "The hearty fat: adipocytes as a source of functional cardiomyocytes" Cardiovascular Research 85:1-2.
Jumabay et al. (2010) "Spontaneously beating cardiomyocytes derived from white mature adipocytes" Cardiovascular Research 85:17-27.
Matsumoto et al. (2007) "Mature Adipocyte-Derived Dedifferentiated Fat Cells Exhibit Multilineage Potential" J Cell Physiol 215(1):210-222.

* cited by examiner

*Primary Examiner* — Thaian N Ton
(74) *Attorney, Agent, or Firm* — Carol L. Francis; Shweta Chandra; Bozicevic, Field & Francis LLP

(57) ABSTRACT

The present invention provides a method of producing progenitor cells, such as cells capable of being differentiated into a plurality of different cell types, from differentiated cells. Methods of using progenitor cells in differentiation and/or tissue or organ repair and/or regeneration and/or building are also provides. Methods of using progenitor cells in treatment and prophylaxis of conditions alleviated by administering stem cells or tissue or organ derived from stem cells to a subject or by grafting stem cells or tissue or organ derived from stem cells into a subject or by transplanting stem cells or tissue or organ derived from stem cells into a subject are also provided. Also included are progenitor cells and differentiated cells and/or tissues and/or organs derived therefrom, and kits comprising same.

13 Claims, No Drawings

METHOD OF PRODUCING ADIPOCYTES FROM FIBROBLAST CELLS

FIELD OF THE INVENTION

The present invention is in the field of medicinal cell biology and more particularly to cell culture, especially the culture of primary cells and cell lines that are differentiated or terminally differentiated. The present invention also relates to methods for producing cells with the ability to differentiate into a plurality of cell types such as for use in medicine and/or veterinary applications and/or for animal improvement.

BACKGROUND OF THE INVENTION

The utility of stem cells (SCs), including hematopoietic SCs, mesenchymal SCs or multipotent adult progenitor cells such as endothelial progenitor cells (EPCs) and embryonic stem cells (ESCs), is well established, especially for generating multiple distinct cell types in medicine and/or veterinary applications and/or for animal improvement.

In particular, stem cells may be used as a source of cells that can be differentiated into various cell types to repopulate damaged cells. For example, joint pain is a major cause of disability, which most often results from damage to the articular cartilage by trauma or degenerative joint diseases such as primary osteoarthritis. Current methods of treatment for cartilage damage are often not successful in regenerating cartilage tissue to a fully functional state, and there is often considerable donor-site rejection. A resolution of this disease state can be provided by regenerating cartilage tissue using stem cells. There are many other tissue degenerative diseases, which can be treated using stem cells, including autoimmune disorders. For example, in the treatment and/or therapy of diabetes, the pancreatic islet cells of a diabetic patient can be regenerated using stem cells that are implanted and/or infused into the patient.

Despite the pluripotency of embryonic stem (ES) cells, legal and moral controversies concerning their use, and the lack of available human ES lines, have prompted researchers to turn to investigating new sources for isolating stem cells from tissues that are not of fetal origin. However, such adult stem cells still involve complicated isolation procedures, and are in limited supply.

Because of the numerous obstacles and technical difficulties in producing and using ES cells and adult stem cells in sufficient quantity for a large number of clinical applications, many researchers are now looking to develop strategies to reprogram somatic cells from adult tissues to thereby create cells having stem cell-like attributes, in particular the ability to differentiate into different cell types.

In one approach, mature cells are fused with embryonic germ cells by a process known as somatic-cell nuclear transfer (SCNT). After fusion, mature cell nuclei display pluripotent properties similar to that of the embryonic germ cells (Tada et al., 1997, EMBO J. 16:6510-6520). This fusion-process essentially returns the mature adult cell to an earlier developmental state (immature state), from which the cell can then mature into differentiated cell types. However, such reprogramming does not escape the requirement for isolated ES-cells or embryonic germ cells. Moreover, the ethical and religious issues associated with using human embryos apply equally to this technology. There are also practical difficulties in SCNT, including the short supply of human oocytes for SCNT.

In another approach, the sequential exposure of primary oligodendrocyte precursor cells (OPCs) to fetal calf serum and basic fibroblast growth factor (bFGF) produces cells that resemble multipotent stem cells (Kondo et al., 2000, Science 289:1754-1757). However, the procedure has not been shown to be applicable to other cells types and, as OPCs are not an abundant cell type, there is limited prospect for the large-scale application of this technology.

Finally, human fibroblasts have been shown to be capable of being made into pluripotent cells by ectopic expression of four factors: Oct3/4, Sox2, Klf4, and c-Myc (Kzutoshi et al., Cell 131:861-872 (2007); Park et al., Nature epub (2007)). The so-called "induced pluripotent stem cells" (iPSCs) produced by this technology were shown to be similar to human embryonic stem (ES) cells in morphology, proliferation, surface antigens, gene expression, epigenetic status of pluripotent cell-specific genes, and telomerase activity. On the other hand, the iPSCs were also shown to give rise to teratomas, raising concerns about the application of the technology to medicine and/or the veterinary industry and/or for animal improvement.

Accordingly, there is a need in the art for an abundant source of cells that are capable of being differentiated into different cell types without extracting or using egg cells or stem cells such as ES cells or the like, and with minimal deleterious effects. More particularly, there is a need in the art for alternative and/or improved methods of culturing differentiated cells and culture media suitable for producing cells capable of differentiating into a plurality of cells types, and which are preferably capable of supporting self-renewal of cells having this capacity. There is also a need for culture systems that permit maintenance of cells capable of differentiating into a plurality of cells types in vitro until the cells are required for subsequent cell or tissue regeneration or repair.

SUMMARY OF THE INVENTION

In work leading up to the present invention, the inventor sought to identify conditions for producing cells having the ability to differentiate into multiple cell types i.e., that could be used as a source of different cell types in a similar manner to mesenchymal stem cells. Against conventional wisdom in the art, the inventor reasoned that the de-differentiation of already-differentiated cells might provide an abundant source of such cells for medical applications e.g., as an "off-the-shelf" supply of stem cell-like cells. The inventor also went against conventional wisdom in not merely seeking to expand existing populations of stems cells from primary tissues, by using differentiated cells as starting material.

As exemplified herein, the inventor has shown that it is possible to produce a cell having the ability to differentiate into a different cell type by culturing human fibroblasts in media having low serum concentration for at least about 2 days, compared to standard culture medium and incubating the cells in the presence of a protease such as trypsin. In this example, both steps are necessary to confer on the cells produced an ability to differentiate into a different cell type.

Accordingly, the present invention provides a method for producing a progenitor cell that is capable of being differentiated into a plurality of different cell types, said method comprising incubating differentiated cells in media comprising a low serum concentration and without supplementation of factors normally present in serum, and detaching the cells, e.g., by incubating the cells in detachment medium comprising a protease or a ligand of a protease activated receptor (PAR).

The order of incubation in low serum medium and detachment is not necessarily essential to the production of cells capable of undergoing subsequent differentiation into a plurality of different cell types. Conveniently, the differentiated cells are incubated in media comprising a low serum concentration and without supplementation of factors normally present in serum before performing detachment.

The term "serum" means the non-cellular liquid phase of blood that remains after coagulation and removal of the blood clot, including blood cells, platelets and fibrinogen. The present invention is not to be limited by the nature of the serum used in low-serum media, the only requirement being that the cells are able to maintain viability in the medium used. In this respect, it is known that normal human fibroblasts require growth factors provided e.g., by fetal bovine serum (FBS) or fetal calf serum (FCS) at about 10% (v/v) for proliferation in culture.

Preferred sera for cell culture are bovine sera e.g., fetal calf serum and fetal bovine serum. Horse sera or artificial sera comprising the constituents of naturally-occurring sera from these sources may also be employed. In another example, in using the cells of the invention in human therapy, preferred sera for cell culture is human sera or artificial sera comprising the constituents of naturally-occurring human sera.

As used herein, the term "low serum concentration" shall be taken to mean a concentration of serum not exceeding about 3% (v/v) in culture medium, preferably not exceeding about 2% (v/v) or about 1% (v/v), and still more preferably, less than 1% (v/v) serum concentration, including serum-free or no serum. Unless the context requires otherwise e.g., by virtue of the addition of a growth factor agonist of the Akt/(PKB) pathway and/or NF-κB pathway, the term "low-serum" shall also be taken to mean conditions in which the concentration of a growth factor supplement in the culture medium is at a level equivalent to or less than the level of the growth factor in serum. In the present context, an alternative low-serum medium includes "artificial sera" or "depleted sera" having low levels of growth factors required for cellular proliferation.

In a particularly preferred example, the term "low serum concentration" shall be taken to mean a concentration of serum between about 0% (v/v) and about 1% serum concentration or an artificial serum or depleted serum having an equivalent or lower level of one or more serum growth factors. Standard methods in cell biology are used to determine the parameters for what constitutes a particular concentration of any serum, including fetal calf serum and bovine serum.

Particularly preferred low-serum media for incubation of the differentiated cells are Dulbecco's Modified Eagle Medium High Glucose (DMEM-HG; e.g., Lonza Cat #12-604), or basal Medium 199 or a modified Medium 199 comprising high glucose. Preferably, the low-serum medium comprises one or more sugars such as glucose, at a concentration of at least about 0.1% (w/v), more preferably at least about 0.2% (w/v) or at least about 0.3% (w/v) or at least about 0.4% (w/v) or at least about 0.5% (w/v) or at least about 0.6% (w/v) or at least about 0.7% (w/v) or at least about 0.8% (w/v) or at least about 0.9% (w/v) or at least about 1.0% (w/v).

Preferably, the differentiated cells are incubated in low-serum media for at least about two days i.e., about 48 hours, and not exceeding about ten days i.e., about 240 hours, including for about two days or about three days or about four days or about five days or about six days or about seven days or about eight days or about nine days or about ten days. More preferably, the cells are incubated in low-serum media for a period between about four days and about nine days, including about four days or about five days or about six days or about seven days or about eight days or about nine days. Still more preferably, the cells are incubated in low-serum media for a period between about five days and about eight days, including about five days or about six days or about seven days or about eight days. As will be apparent from the disclosure herein, lower numbers of progenitor cells may be apparent with shorter periods of exposure of the cells to low serum media than are observed for optimum periods of incubation in low serum media, however such sub-optimum incubation conditions are clearly within the scope of the invention.

Alternatively, or in addition, the cells are incubated in low-serum medium for a period of time sufficient for the level of one or more gene products of the cells that delay or inhibit or repress cell cycle progression or cell division to be expressed de novo or at an increased level in the cells, such as, for example, the cell cycle proteins p27Kip1 and/or p57Kip2 and/or p18. These proteins are expressed in fibroblasts and down-regulated before the onset of cell division.

As used herein, the term "detachment" or variations such as "detaching the cells" or "cell detachment" shall be taken to include any method of detaching cells from each other and/or from a surface of a culture vessel in which they are maintained known in the art. In one example, the cells are incubated in a detachment medium comprising a protease or PAR ligand for a time and under conditions sufficient for the cells to detach from each other and/or from a surface of a culture vessel in which they are maintained or to become rounder in appearance. By "PAR ligand" or equivalent term is meant a ligand capable of activating a protease-activated receptor, such as PAR-1 and/or PAR-2 and/or PAR-3 and/or PAR4. Without being bound by any theory or mode of action, incubation in a protease or PAR ligand for a time and under conditions sufficient to detach the cells, or for their appearance to be modified in this manner, is sufficient for a partial or complete breakdown of integrins that normally mediate cell adhesion or at least for the promotion of cellular signalling pathways mediated by an integrin.

Alternatively, or in addition, the cells are incubated in a detachment medium comprising a protease or PAR ligand for a time and under conditions sufficient for activation of one or more protease-activated receptors (PARs) such as PAR-1 and/or PAR-2 and/or PAR-3 and/or PAR4 to occur.

Preferred proteases and PAR ligands for performing the invention include chymotrypsin, trypsin, thrombin, pepsin, papain, matrix-metalloproteinase (MMP) and a PAR-2-activating peptide comprising the sequence SLIGRL. More preferably, the protease is trypsin, thrombin, plasmin, or a PAR-2-activating peptide comprising the sequence SLIGRL. In a particularly preferred example, trypsin is employed.

In another example, the cells are detached from each other Preferred proteases and PAR and/or from a surface of a culture vessel in which they are maintained or become rounder in appearance by incubating the cells in a $Ca^{2+}$-free and $Mg^+$-free detachment medium comprising ethylenediaminetetraacetic acid (EDTA) for a time and under conditions sufficient for detachment of integrins from the cellular matrix. In a further example, cells are detached from each other and/or from a surface of a culture vessel in which they are maintained or become rounder in appearance by incubating the cells in a detachment medium comprising citric saline for a time and under conditions sufficient for detachment of the cells and/or integrins from the cellular matrix.

In one example, the method of the present invention further comprises incubating the cells under high cell-density conditions. In accordance with this example, a high density plating medium is employed. As used herein, the term "high density plating medium" means any cell medium capable of supporting progenitor cells produced by the method of the present invention. In one example progenitor cells produced by the method of the invention undergo minimal or no cell division when cultured, maintained or incubated in the high density plating medium. Exemplary high density plating medium includes Medium-199 comprising 170 nM insulin, 0.5 mM 3-isobutyl-1-methylxanthine, 0.2 mM indomethacin, 1 µM dexamethasone, and 15% rabbit serum. Alternatively, high density plating medium includes Dulbecco's Modified Eagle Medium (DMEM) or basal Medium 199 supplemented with 10% fetal calf serum (FCS). However other media may be employed.

Conveniently, the differentiated cells are incubated in a low-serum media, and subjected to one or more means of achieving their detachment, before being incubated under high cell density conditions.

An advantage of incubating cells at high cell density conditions in concert with serum deprivation of differentiated cells and detachment of the cells, is that the proportion of progenitor cells capable of being differentiated into a plurality of different cell types is increased.

As used herein, the term "high density" or similar term such as "high density conditions" or "high cell density conditions" shall be taken to mean that the cells are maintained, cultured or incubated until confluence or cell-to-cell contact is achieved or at a starting density of cells of about 50,000 cells to about 200,000 cells per standard-size culture well/plate, including about 60,000 cells or greater per standard-size culture well/plate, or about 70,000 cells or greater per standard-size culture well/plate, or about 80,000 cells or greater per standard-size culture well/plate, or about 90,000 cells or greater per standard-size culture well/plate, or about 100,000 cells or greater per standard-size culture well/plate, or about 200,000 cells per standard-size culture well/plate. Higher cell densities above about 200,000 cells per standard-size culture well/plate may also be employed. By "standard-size" in this context is meant about 27 $mm^2$ plating surface area in a well or plate:

Alternatively or in addition, high density conditions include the maintenance, culture or incubation of cells at a starting density of cells of about 1500 cells/$mm^2$ plating surface area to about 10,000 cells/$mm^2$ plating surface area, including about 1,850 cells/$mm^2$ surface area of the culture vessel or greater, or about 2,220 cells/$mm^2$ surface area of the culture vessel or greater, or about 2,590 cells/$mm^2$ surface area of the culture vessel or greater, or about 2,960 cells/$mm^2$ surface area of the culture vessel or greater, or about 2,220 cells/$mm^2$ surface area of the culture vessel or greater, or about 3,330 cells/$mm^2$ surface area of the culture vessel or greater, or about 3,703 cells/$mm^2$ surface area of the culture vessel surface area of the culture vessel or greater, or about 7,407 cells/$mm^2$ surface area of the culture vessel surface area of the culture vessel or greater.

In another example, cells are incubated under high density conditions e.g., until confluence or cell-to-cell contact is achieved, before detaching the cells. Such cells may be subsequently seeded at any density e.g., on a biocompatible matrix or in culture medium such as to promote their differentiation.

The optimum period of maintenance, culture or incubation in high density plating medium is determined empirically e.g., by calculating the optimum number of differentiated cells produced from aliquots of progenitor cells incubated at high density over a time course and subsequently incubated under conditions sufficient for differentiation to occur. Alternatively, or in addition, the optimum period of maintenance, culture or incubation in high density plating medium is determined empirically e.g., by determining fibroblast-specific and/or progenitor cell-specific marker expression by aliquots of progenitor cells incubated at high density over a time course. Alternatively, or in addition, the optimum period of maintenance, culture or incubation in high density plating medium is a period of time until adherence is achieved i.e., a shorter time than required for cells to become adherent. Alternatively, or in addition, the optimum period of maintenance, culture or incubation in high density plating medium is up to about 5 days, including up to about 4 days or up to about 3 days or up to about 2 days or up to about 1 day i.e., up to about 24 hours.

In another example of the invention, cells are introduced to high density culture conditions within about 6 hours to about 10 hours from their detachment, including within about 6 hours to about 9 hours from their detachment, or within about 6 hours to about 8 hours from their detachment, or within about 6 hours to about 7 hours from their detachment. In another example, cells are introduced to high density culture conditions within about 1 hour to about 6 hours from their detachment, including within about 5 hours to about 6 hours from their detachment, or within about 4 hours to about 5 hours from their detachment, or within about 3 hours to about 4 hours from their detachment, or within about 2 hours to about 3 hours from their detachment, or within about 1 hours to about 2 hours from their detachment. In another example, cells are introduced to high density culture conditions in less than about 5 hours from their detachment, including less than about 4 hours from their detachment, or less than about 3 hours from their detachment, or less than about 2 hours from their detachment, or less than about 1 hour from their detachment. In yet another example, the differentiated cells are incubated in a low-serum media, subjected to one or more means of achieving their detachment, and simultaneously introduced to high density culture conditions.

It will be apparent from the disclosure herein that similar, equivalent or improved results e.g., in terms of numbers of progenitor cells capable of being differentiated into a plurality of different cell types and/or in terms of the degree of multipotency and/or pluripotency of the progenitor cells produced, are able to be produced by agonism of the Akt/(PKB) pathway and/or NF-kB pathway. Without being bound by any theory or mode of action, the inventor reasoned that the time required for low serum incubation to induce optimum plasticity of fibroblasts coincided with the time course for induction of the Akt/(PKB) and/or NF-kB pathway(s), and that the responses of cells to the combined low-serum and detachment, and optional high density maintenance, culture or incubation conditions, are likely to induce one or both pathways.

Accordingly, an alternative example of the present invention provides a method for producing a progenitor cell that is capable of being differentiated into a plurality of different cell types, said method comprising incubating differentiated cells in media comprising an amount of an agonist or partial agonist of the Akt/(PKB) pathway and/or NF-kB pathway and for time sufficient to render the cells capable of being differentiated into a plurality of different cell types.

This example of the invention is performed on cultured cells ex vivo. In accordance with this example, it is preferred that the method comprises the first step of obtaining isolated cells from a suitable source e.g., from a commercial supplier.

Alternatively, the cells have been isolated previously from a human or animal subject, including a syngeneic subject to whom progenitor cells produced by the method can optionally be administered e.g., topically, systemically, locally as an injectable and/or transplant and/or device, or in conjunction with one or more treatments for injuries, allografts or autografts.

Alternatively, or in addition, an intermediate step of cell expansion in culture may be performed to increase the number of progenitor cells. Cell expansion in culture may be performed, for example, prior to administration of cells to a subject.

Preferred agonists of the Akt/(PKB) pathway suitable for this purpose are described herein and include e.g., interleukin-1 (IL-1), platelet derived growth factor (PGDF-BB), insulin growth factor (IGF-1), transforming growth factor-beta (TGF-β), nerve growth factor (NGF) and carbachol or any active fragment or active chemical group thereof.

Preferred agonists of the NF-κB pathway suitable for this purposes are described herein and include e.g., tumor necrosis factor-alpha (TNF-α), interleukin 1 (IL-1), or any active fragment thereof, lysophosphatidic acid (LPA) or lipopolysaccharide (LPS).

Preferably, the cells are incubated in the presence of an agonist of the Akt/(PKB) pathway and/or NF-κB pathway in low serum-comprising media or serum-free media to achieve optimum plasticity and/or multipotency or pluripotency. Such incubation is preferably for a time and under conditions sufficient to induce the Akt/(PKB) pathway and/or NF-κB pathway in the cells or a component thereof that is sufficient to render the cells capable of being differentiated into a plurality of different cell types.

In one example, the cells are further incubated or maintained on low-serum medium, and without supplementation of factors normally present in serum, e.g., before, during or following incubation in the presence of one or more agonists of the Akt/(PKB) pathway and/or one or more agonists of the NF-κB pathway. Such additional incubation is for at least about two days i.e., about 48 hours, and not exceeding about ten days i.e., about 240 hours, including for about two days or about three days or about four days or about five days or about six days or about seven days or about eight days or about nine days or about ten days. More preferably, the cells are incubated in low-serum media for a period between about five days and about nine days, including about five days or about six days or about seven days or about eight days or about nine days. Still more preferably, the cells are incubated in low-serum media for a period between about six days and about eight days, including about six days or about seven days or about eight days. In performing such examples, the agonist of the Akt/(PKB) pathway and/or NF-κB pathway may be added to the low-serum medium at any time point in the incubation period of at least about four days and not exceeding about ten days, or a shorter time as indicated herein. The skilled artisan is able to determine appropriate points for addition of one or more agonists to the medium without undue experimentation, and all such routine variations are within the scope of the present invention.

In another example, the cells are further detached by any means known in the art e.g., before, during or following incubation in the presence of one or more agonists of the Akt/(PKB) pathway and/or one or more agonists of the NF-κB pathway. Where low-serum medium is employed, is it preferred for such detachment to follow low-serum incubation. As will be apparent from the preceding disclosure, the cells may be detached by incubation in media comprising a protease or a ligand of a protease activated receptor (PAR). Alternatively, the cells are detached by incubation in a $Ca^{2+}$-free and $Mg^+$-free media comprising EDTA. Alternatively, the cells are detached by incubation in a media comprising citric saline.

In another example, the cells are maintained, incubated or cultured under high density conditions e.g., after detachment and in a medium capable of supporting differentiation of progenitor cells, or prior to detachment. Such incubation may be before, during or following incubation in the presence of one or more agonists of the Akt/(PKB) pathway and/or one or more agonists of the NF-κB pathway.

In a further example, the cells are incubated in low-serum medium and detached and wherein one or more agonists of the Akt/(PKB) pathway and/or one or more agonists of the NF-κB pathway is included in low serum medium and/or in detachment medium. Alternatively, differentiated cells may be treated with one or more agonists of the Akt/(PKB) pathway and/or one or more agonists of the NF-κB pathway before commencing low-serum incubation and/or following detachment.

In a further example, the cells are incubated in low-serum medium, detached and maintained, incubated or cultured under high density conditions wherein one or more agonists of the Akt/(PKB) pathway and/or one or more agonists of the NF-κB pathway is included in low serum medium and/or in detachment medium and/or high density plating medium. Alternatively, differentiated cells may be treated with one or more agonists of the Akt/(PKB) pathway and/or one or more agonists of the NF-κB pathway before commencing low-serum incubation and/or following high density culture.

It is to be understood that the ordering of the incubation with protease or a ligand of a protease activated receptor (PAR), and the incubation in the presence of the agonist(s), with or without extended incubation in low serum medium for about two days to about ten days or shorter periods, and optionally combined with high density incubation, is not necessarily essential to the production of cells capable of undergoing subsequent differentiation into a plurality of different cell types. Conveniently, the differentiated cells are incubated in media comprising one or more agonists of the Akt/(PKB) pathway and/or one or more agonists of the NF-κB pathway before detachment of the cells for example by incubating the cells in media comprising a protease or a ligand of a protease activated receptor (PAR).

In accordance with this example, it is preferred for cells produced ex vivo to be formulated for use topically, systemically, or locally as an injectable and/or transplant and/or device, usually by adding necessary buffers. Alternatively, the cells are administered or formulated for use in conjunction with one or more treatments for injuries, allografts or autografts, to enhance wound repair and/or tissue regeneration.

In another example, the present invention provides a method for producing a progenitor cell that is capable of being differentiated into a plurality of different cell types, said method comprising incubating differentiated cells in situ with an amount of an agonist or partial agonist of the Akt/(PKB) pathway and/or NF-κB pathway and for time sufficient to render the cells capable of being differentiated into a plurality of different cell types.

This example of the invention is performed on a human or animal subject in situ e.g., without obtaining isolated cells or performing an intermediate cell expansion in culture.

In accordance with this example, the agonist or partial agonist of the Akt/(PKB) pathway and/or agonist of the NF-kB pathway is(are) administered directly to a body site in the patient or in the vicinity of a body site in the patient in need of progenitor cells. Such tissue includes without limitation tissue in need of repair such as, for example, an injury, wound, burn, inflamed tissue, degenerated or damaged nerve, artery, muscle, bone, cartilage, fat, tendon, ligament, muscle or marrow stroma and combinations thereof.

Preferred agonists of the Akt/(PKB) pathway suitable for this purpose are described herein and include e.g., interleukin-1 (IL-1), platelet derived growth factor (PGDF-BB), insulin growth factor (IGF-1), transforming growth factor-beta (TGF-β), nerve growth factor (NGF) and carbachol or any active fragment or active chemical group thereof.

Preferred agonists of the NF-κB pathway suitable for this purposes are described herein and include e.g., tumor necrosis factor-alpha (TNF-α), interleukin 1 (IL-1), or any active fragment thereof, lysophosphatidic acid (LPA) or lipopolysaccharide (LPS).

Preferably, the agonist of the Akt/(PKB) pathway and/or NF-κB pathway is administered to the site in need thereof for a time and under conditions sufficient to achieve optimum plasticity and/or multipotency or pluripotency of differentiated cells at that site. Such incubation is preferably for a time and under conditions sufficient to induce the Akt/(PKB) pathway and/or NF-κB pathway in the cells or a component thereof that is sufficient to render the cells capable of being differentiated into a plurality of different cell types. The skilled artisan is able to determine appropriate conditions for treatment with one or more agonists without undue experimentation, and all such routine variations are within the scope of the present invention.

Preferably, the method further comprises administering a protease or a ligand of a protease activated receptor (PAR) to the site in need of progenitor cells. Without being bound by any theory or mode of action, the administration of a protease or PAR ligand promotes de-differentiation of differentiated cells and/or detachment of integrins from the extracellular matrix, thereby permitting the progenitor cells to enter circulation and regenerate damaged cells and tissues in situ.

It is to be understood that the ordering of the incubation with protease or a ligand of a protease activated receptor (PAR), and the incubation in the presence of the agonist(s), is not necessarily essential to the production of cells at the body site capable of undergoing subsequent differentiation into a plurality of different cell types. Conveniently, one or more agonists of the Akt/(PKB) pathway and/or one or more agonists of the NF-κB pathway are administered to the body site before administering a protease or a ligand of a protease activated receptor (PAR).

Preferred differentiated cells on which the present invention is performed according to any example hereof include e.g., primary cells and immortalized cell lines. It is to be understood that the differentiated cells may also be terminally differentiated cells. The only requirement for such cells in performing this example of the invention is that they do not undergo apoptosis during the period of incubation in low serum media, especially serum-free media. However, as indicated in the examples, cells that normally undergo apoptosis during prolonged exposure to serum-free or low-serum media can be used in other examples of the invention employing one or more agonists of the Akt/(PKB) pathway and/or NF-κB pathway to shorten the induction period required to induce plasticity in the starting cells.

Cells of human origin, or potentially cells of porcine origin, are preferred for medical applications. More preferably the cells are derived from a tissue of a subject to whom a downstream product thereof is to be administered i.e., they are autologous.

For veterinary or animal improvement purposes, the cells may be derived from any animal species in which they would be compatible when administered. Cells from any commercially-important animal species are contemplated herein e.g., pigs, cattle, horses, sheep, goats, dogs, cats, etc. As with human applications, it is preferred to use autologous cells for such applications to minimize rejection.

Exemplary differentiated cells for use in the present invention include skin cells, epidermal cells, fibroblasts, keratinocytes, melanocytes, epithelial cells, neural cells such as those derived from the peripheral nervous system (PNS) and central nervous system (CNS), glial cells, Schwann cells, astrocytes, oligodendrocytes, microglial cells, lymphocytes, T cells, B cells, macrophages, monocytes, dendritic cells, Langerhans cells, eosinophils, adipocytes, cardiac muscle cells, osteoclasts, osteoblasts, endocrine cells, β-islet cells, endothelial cells, granulocytes, hair cells, mast cells, myoblasts, Sertoli cells, striated muscle cells, zymogenic cells, oxynitic cells, brush-border cells, goblet cells, hepatocytes, Kupffer cells, stratified squamous cells, pneumocytes, parietal cells, podocytes, synovial cells, serosal cells, pericytes, osteocytes, Purkinje fiber cells, myoepithelial cells, or megakaryocytes.

Chondrocytes can also be used in the present invention for those examples that specifically require low serum incubation conditions.

In a particularly preferred example, the cells are fibroblasts, preferably of dermal origin.

It will be apparent from the disclosure herein that, in performing the present invention, the differentiated cell is not merely reprogrammed from one developmental pathway to another developmental pathway, but that a progenitor cell is produced that can be stored or otherwise maintained until required for downstream processing e.g., to give rise to different cell types. Without compromising the generality of the present invention, the method of the invention thus produces cells having one or more stem-cell like attributes in so far as they are multipotent, pluripotent or totipotent progenitor cells. For example, the cells produced in accordance with the invention are a novel population of stem cells e.g., having undetectable or low (negligible) levels of at least one and preferably a plurality of the following cell markers as determined by standard cell marker detection assays: CD90, CD117, CD34, CD113, FLK-1, tie-2, Oct 4, GATA-4, NKx2.5, Rex-1, CD105, CD117, CD133, MHC class I receptor and MHC class II receptor. By the term "standard cell marker detection assay" is meant a conventional immunological or molecular assay formatted to detect and optionally quantify one of the foregoing cell markers (i.e., CD90, CD117, CD34 etc.). Examples of such conventional immunological assays include Western blotting, ELISA, and RIA. Preferred antibodies for use in such assays are provided below. See generally, Harlow and Lane in Antibodies: A Laboratory Manual, CSH Publications, N.Y. (1988), for disclosure relating to these and other suitable assays. Particular molecular assays suitable for such use include polymerase chain reaction (PCR) type assays using oligonucleotide primers e.g., as described in WO 92/07075 and/or Sambrook et al. in Molecular Cloning: A Laboratory Manual (2d ed. 1989) and/or Ausubel et al., Current Protocols in Molecular Biology, John Wiley & Sons, New York, 1989.

Accordingly, in a further example, the present invention provides a method for producing a progenitor cell that is capable of being differentiated into a plurality of different cell types, said method comprising incubating differentiated cells in media comprising a low serum concentration and without supplementation of factors normally present in serum, detaching the cells, and optionally incubating the cells under high density conditions, preferably in a high density plating medium to thereby render the cells capable of being differentiated into a plurality of different cells types, and maintaining or storing the cells as progenitor cells.

In a further example, the present invention provides a method for producing a progenitor cell that is capable of being differentiated into a plurality of different cell types, said method comprising incubating differentiated cells in media comprising an amount of an agonist or partial agonist of the Akt/(PKB) pathway and/or NF-κB pathway and for time sufficient to render the cells capable of being differentiated into a plurality of different cell types, and maintaining or storing the cells as progenitor cells.

Preferably, the method according to any example hereof further comprises providing the differentiated cells e.g., as an adherent cell culture.

In a further example, the present invention further comprises genetically engineering the progenitor cells to express a protein of interest, such as for example, a macromolecule necessary for cell growth, morphogenesis, differentiation, or tissue building and combinations thereof, and preferably, a bone morphogenic protein, a bone morphogenic-like protein, an epidermal growth factor, a fibroblast growth factor, a platelet derived growth factor, an insulin like growth factor, a transforming growth factor, a vascular endothelial growth factor, Ang-1, PIGF and combinations thereof.

In a further example, the present invention encompasses a cell culture comprising progenitor cells produced by the method disclosed according to any example hereof. Preferably, the cell culture is for treatment of the human or animal body by therapy or prophylaxis.

It will also be apparent from the disclosure herein that the stem cell-like attribute of the progenitor cells produced in accordance with the inventive method confer the ability to produce one or more cells or tissues from them in medical and veterinary applicants and for animal improvement. In this respect, methods for producing such different cell types from a unipotent, multipotent, pluripotent or totipotent progenitor cells are known in the art and/or described herein.

Accordingly, a further example of the present invention provides a process for producing a differentiated cell, said process comprising producing a progenitor cell according to any example of the invention hereof and then incubating the progenitor cell for a time and under conditions sufficient to induce differentiation of the progenitor cell into a differentiated cell.

The progenitor cells may be used to produce any cell type. For example, the differentiated cell produced by the process may be a skin cell, epidermal cell, keratinocyte, melanocyte, epithelial cell, dopaminogenic cell, neural cell, glial cell, Schwann cell, astrocyte, oligodendrocyte, microglial cell, blood cell, lymphocyte, T cell, B cell, macrophage, monocyte, dendritic cell, lagerhans cell, eosinophil, adipocyte, cardiomyocyte, cardiac muscle cell, cardiac fibroblast, osteoclast, osteoblast, endocrine cell, β-islet cell, insulin secreting cell, endothelial cell, epithelial cell, granulocyte, hair cell, mast cell, myoblast, Sertoli cell, striated muscle cell, zymogenic cell, oxynitic cell, brush-border cell, goblet cell, hepatocyte, Kupffer cell, stratified squamous cell, pneumocyte, parietal cell, podocyte, synovial cell, serosal cell, pericyte, chondrocyte, osteocyte, Purkinje fiber cell, myoepithelial cell, megakaryocyte, etc.

As with the progenitor cells of the invention, such differentiated cells can be maintained by one or a combination of strategies including those involving maintenance in vitro. The differentiated cells can be maintained by strategies including those involving maintenance ex vivo and/or in vivo.

Accordingly, in a further example, the present invention encompasses a cell culture comprising differentiated cell produced from a progenitor cell in accordance with the process disclosed according to any example hereof. Preferably, the cell culture is for treatment of the human or animal body by therapy or prophylaxis.

In another example the progenitor cells may used to differentiate into tissues and/or organs. According to this example, the progenitor cells produced by the method of the invention and/or the differentiated cells derived there from may be used for regenerating and/or building any tissue or organ. For example, the regenerated or built tissue produced by the process includes a skin tissue, an epidermal tissue, a keratinocyte tissue, a melanocyte tissue, an epithelial, a dermal dendrocyte tissue, a nervous tissue, a muscle tissue, a connective tissue, a mucosal tissue, a cardiac tissue, a cardiac muscle tissue, a cardiomyocyte tissue, a cardiac fibroblast tissue, an endocrine tissue, an adipose tissue, a galial tissue, a collagen or fibrin tissue, an osseous or bone tissue, an osteocyte tissue, a blood vessel tissue e.g., an endothelial tissue, a lymphoid tissue, an endocrine tissue e.g., a pancreatic endocrine tissue, an islet tissue e.g., β-islet tissue, a chondrocyte tissue, a hepatic tissue, a eosinophil tissue, an osteoblast tissue, an osteoclast tissue, a hair tissue, a bone marrow tissue, a striated muscle tissue, a reproductive tissue, a synovial tissue, etc. For example, the organ regenerated or produced by the process includes trachea, skin, hair, liver, spleen, heart, kidney, muscle, bone, a limb such as a finger and/or toe and/or arm and/or leg, nose, ear, panaceas, lung, lymphoid organ, female or male reproductive organ e.g., ovary and/or testis, uterus, vagina, cervix, and fallopian tubes, nerve, blood vessel, small intestine, large intestine, endocrine organ or hormone-secreting gland e.g., pituitary gland, bladder, dental tissues such as teeth, or dentin, etc.

Accordingly in a one example, the present invention further provides a method of regenerating, repairing and/or building a tissue and/or an organ, said method comprising culturing or perfusing the progenitor cells produced according to any example hereof and/or culturing differentiated cells derived from said progenitor cells on or into a biocompatible scaffolding material or matrix. In one example, the scaffold material or matrix, provides the mitogens and/or biological signalling suitable for promoting or enhancing differentiation of the progenitor cells, and/or tissue building repair or regeneration and/or organ building, repair or regeneration. In another example, the scaffold material or matrix provides the structure or outline to a tissue to be repaired, regenerated or built, and/or organ to be repaired, regenerated or built. Such scaffold material or matrix may include for example a non-cellular matrix comprising proteoglycan and/or collagen or other suitable material for tissue building or organ building processes to occur. In one example, the scaffold material or matrix comprises synthetic or semi-synthetic fibers such as Dacron™, Teflon™ or Gore-Tex™.

In another example, the scaffold material or matrix comprises a decellularized organ or tissue stripped of its cells by any means known in the art.

In one example, tissue and/or organ regeneration, repair or building occurs in vitro externally of the body of an organism, including a human or other mammalian subject in need thereof. In another example, the tissue and/or organ regeneration, repair or building occurs in vivo in an organism, including a human or other mammalian subject in need thereof.

In one example, tissue regeneration or repair or building is used to reduce or eliminate scar tissue.

In one example, the present invention conveniently utilizes a starter cell, i.e., any differentiated primary cell, cell strain, or cell line that is derived and/or obtained from the same tissue type and/or organ type as the tissue and/or organ which is being regenerated, repaired and/or built. For example, skin fibroblasts from a limb or an appendage are used to produce progenitor cells that are subsequently regenerated into a limb or an appendage e.g., a finger, a toe, an arm or a leg.

A further example of the present invention provides for the use of a progenitor cell produced according to any example hereof or a differentiated cell or tissue or organ derived there from in the prophylactic or therapeutic treatment of the human or animal body.

In a further example, the present invention provides for the use of a progenitor cell produced according to any example hereof or a differentiated cell or tissue or organ derived there from in the preparation of a cell preparation for the prophylactic or therapeutic treatment of a condition in a subject alleviated by administering stem cells or tissue derived from stem cells to a subject or by grafting stem cells or tissue derived from stem cells into a subject or by transplanting stem cells or tissue derived from stem cells into a subject.

In a further example, the present invention provides for the use of an isolated, non-culture progenitor cell in the preparation of a medicament for administration to a subject, wherein the non-culture progenitor cell is obtained via a method of the invention according to any example hereof. By "non-culture progenitor cell" is meant a progenitor cell of the present invention produced without cell expansion in vitro and preferably used within about twenty four hours following their preparation by a method described herein according to any example.

In a further example, the present invention provides for the use of an isolated, non-culture progenitor cell in the preparation of a medicament for stimulating or enhancing tissue repair in a subject, wherein the non-culture progenitor cell is obtained via a method of the invention according to any example hereof.

In a further example, the present invention provides for the use of an isolated, non-culture progenitor cell in the preparation of a medicament for stimulating or enhancing tissue formation in a subject, wherein the non-culture progenitor cell is obtained via a method of the invention according to any example hereof.

Preferably, the differentiated cells, tissues or organs are introduced to the human or animal body by grafting means, and it is clearly within the scope of the present invention to provide a graft that includes isolated progenitor cells or differentiated cells or tissues or organs derived there from.

As used herein, the term "graft" shall be taken to mean a cell or tissue or organ preparation that includes an isolated progenitor cell produced in accordance with any example of the invention hereof and/or a differentiated cell, tissue or organ derived in vitro or in vivo from said isolated progenitor cell and, optionally comprising one or more other cells and/or mitogens and/or a matrix suitable for promoting or enhancing differentiation and/or tissue building, repair or regeneration and/or organ building, repair or regeneration. For example, a "graft" includes tissue or organ that is produced by culturing progenitor cells of the invention and/or differentiated cells derived from said progenitor cells onto a matrix e.g., a non-cellular matrix comprising proteoglycan and/or collagen or other suitable material for tissue building or organ building processes to occur e.g., synthetic or semi synthetic fibers that give structure to a graft, such as Dacron™, Teflon™ or Gore-Tex™. By "graft" is also meant progenitor cells of the invention that have been administered to a recipient and become part of one or more tissues or organs of that recipient. A graft of the invention may also take the form of a tissue preparation or tissue culture preparation in which progenitor cells of the invention have been combined with other cells and/or mitogens to promote differentiation and/or cell replication that produces an intended graft. If desired, the preparation can be combined with synthetic or semi synthetic fibers to give structure to the graft. Fibers such as Dacron™, Teflon™ or Gore-Tex™ are preferred for certain applications. Sometimes the word "engraftment" will be used to denote intended assimilation of the progenitor cells or derivative differentiated cells tissue or organs into a target tissue, organ or organism, including a human or other mammalian subject. Preferred engraftment involves neural tissue, cardiovascular tissue, cardiac tissue, splenic tissue, pancreatic tissue, etc.

In using the cells of the invention for medical applications or veterinary applications, or in animal improvement, immunological relationship between a donor of the differentiated cells used to produce the progenitor cells, and the recipient of the progenitor cells or a cell or tissue or organ derived from the progenitor cells, can be allogenic, autologous, or xenogeneic as needed. In preferred examples, the donor and recipient will be genetically identical and usually will be the same individual (syngeneic). In this instance, the graft will be syngeneic with respect to the donor and recipient. In one example, the progenitor cells and/or graft will be immune tolerated in the recipient subject.

A further example of the present invention provides a method for preventing, treating or reducing the severity of a disease or disorder in a human or animal subject said method comprising administering to the human or animal subject in need of treatment at least one isolated progenitor cell or graft or a combination thereof. Preferably, the administration is sufficient to prevent, treat or reduce the severity of the disease or disorder in the human or animal subject.

In one example, the method further includes incubating the cells or graft in the human or animal subject for at least about a week, preferably between from about two to eight weeks. It will be apparent to those working in the field that the incubation period is flexible and can be extended or shorten to address a particular indication or with respect to the health or age of the individual in need of treatment. Typical amounts of progenitor cells to use will depend on these and other recognized parameters including the disease to be treated and the speed of recovery needed. However for most applications between from about $1\times10^3$ to about $1\times10^7$ progenitor cells per grafting site will suffice, typically about $1\times10^5$ of such cells. Cells may be administered by any acceptable route including suspending the cells in saline and administering same with a needle, stent, catheter or like device. In examples in which myocardial ischemia or an infarct is to be addressed, the administration will be a bolus injection near or directly into the desired site.

In another example, the method further includes administering to the human or animal subject in need of treatment at least one growth factor or mitogen or functional fragment thereof to promote tissue regeneration or cellular proliferation. Alternatively, or in addition, the method can include administering to the mammal at least one nucleic acid encoding at least one growth factor or mitogen or functional fragment thereof. For example, methods for administering such nucleic acids to mammals have been disclosed by U.S. Pat. No. 5,980,887 and WO 99/45775.

In yet another example, the method further includes administering to the human or animal subject one or more other progenitor cells.

Further provided by the invention is a pharmaceutical product for preventing, treating or reducing the severity of a disease or disorder, said composition comprising a population of progenitor cells or graft produced according to any example hereof and a pharmaceutically acceptable carrier. Optionally, the composition comprises directions for preparing, maintaining and/or using the progenitor cells or graft, including any cell culture, tissue or organ. In one example, the product further includes at least one growth factor or mitogen or functional fragment thereof. In another example, the product further comprises at least one nucleic acid encoding a growth factor, mitogen or functional fragment thereof.

Further provided by the invention is a kit for building, repairing or regenerating a tissue or an organ, said kit comprising a population of progenitor cells produced according to any example hereof and a scaffold or matrix for culturing the progenitor cells or differentiated cells produced from said progenitor cells. Optionally, the composition comprises directions for preparing, maintaining and/or using the progenitor cells or graft, including any cell culture, tissue or organ. In one example, the product further includes at least one growth factor or mitogen or functional fragment thereof. In another example, the product further comprises at least one nucleic acid encoding a growth factor, mitogen or functional fragment thereof.

Further provided by the invention is an isolated differentiated cells derived from progenitor cells produced according to any example hereof. Also provided by the invention is a scaffold or matrix comprising progenitor cells or one or more populations of differentiated cells derived from the progenitor cells as described according to any example hereof. Further provided by the invention is any tissue or any organ derived in vitro or in vivo from isolated progenitor cells produced according to any example hereof or any tissue or any organ derived in vitro or in vivo from differentiated cells derived from the progenitor cells as described according to any example hereof.

Accordingly, in one example the present invention provides a method for producing a progenitor cell capable of being differentiated into a plurality of different cell types, said method comprising incubating differentiated cells in a low-serum medium comprising a low serum concentration and without supplementation of factors normally present in serum, and detaching the cells, wherein said method produces progenitor cells capable of being differentiated into a plurality of different cell types.

In one example, the differentiated cells are animal cells.

In one example, the differentiated cells are fibroblasts or chondrocytes.

In one example, the progenitor cells are capable of being differentiated into a cell type selected from the group consisting of a skin cell, an epidermal cell, a keratinocyte, a melanocyte, an epithelial cell, a neural cell, a dopaminogenic cell, a glial cell, a Schwann cell, an astrocyte, an oligodendrocyte, a microglial cell, a blood cell, a lymphocyte, a T cell, a B cell, a macrophage, a monocyte, a dendritic cell, a Lagerhans cell, an eosinophil, an adipocyte, a cardiomyocyte, a cardiac muscle cell, a cardiac fibroblast, an osteoclast, an osteoblast, an endocrine cell, a β-islet cell, an insulin secreting cell, an endothelial cell, an epithelial cell, a granulocyte, a hair cell, a mast cell, a myoblast, a Sertoli cell, a striated muscle cell, a zymogenic cell, an oxynitic cell, a brush-border cell, a goblet cell, a hepatocyte, a Kupffer cell, a stratified squamous cell, a pneumocyte, a parietal cell, a podocyte, a synovial cell, a serosal cell, a pericyte, a chondrocyte, an osteocyte, a Purkinje fiber cell, a myoepithelial cell and a megakaryocyte.

In one example, the low-serum medium does not exceed about 3% (v/v) total serum concentration.

In one example the method comprises incubating the differentiated cells in low-serum medium for at least about 2 days and not exceeding about 10 days.

In another example the method comprises incubating the differentiated cells for a period of time sufficient to induce and/or increase expression of one or more gene products that delay or inhibit or repress cell cycle progression.

In one example, the one or more gene products that delay or inhibit or repress cell cycle progression are selected from $p27^{Kip1}$, $p57^{Kip2}$ and p18.

In one example, the method comprises detaching the cells by incubating the cells in a medium comprising a protease and/or incubating cells expressing one or more protease activated receptors (PARs) with one or more PAR ligands.

In one example, the protease is selected from the group consisting of chymotrypsin, trypsin, thrombin, pepsin, papain and matrix-metalloproteinase (MMP).

In one example, a PAR is selected from the group consisting of PAR-1, PAR-2, PAR-3 and PAR4.

In another example, a PAR ligand comprises a PAR-2-activating peptide comprising the sequence SLIGRL.

In another example, the method comprises detaching the cells by incubating the cells in a medium comprising EDTA, wherein said medium is substantially $Ca^{2+}$-free and substantially $Mg^+$-free so as to not interfere with detachment.

In yet another example, the method comprises detaching the cells by incubating the cells in a medium comprising a salt of citric acid.

In on example, the method comprises incubating differentiated cells in a low-serum medium before detaching the cells.

In another example, the method comprises incubating differentiated cells in a low-serum medium after detaching the cells.

In one example, said method further comprises incubating the cells in media comprising an agonist or partial agonist of the Akt/(PKB) pathway.

In one example, said method further comprises incubating the cells in media comprising an agonist or partial agonist of the NF-kB pathway.

In one example, said method further comprises incubating or maintaining or culturing the cells in high cell-density conditions.

In one example, incubating or maintaining or culturing the cells in high cell-density conditions comprising incubating or maintaining or culturing the cells until confluence or cell-to-cell contact is achieved.

In another example, the high cell-density conditions comprise a minimum density between about 1500 cells/mm$^2$ plating surface area to about 10,000 cells/mm$^2$ plating surface area.

In yet another example, the method comprises incubating and/or maintaining and/or culturing the cells in high cell-density conditions for a shorter time than required for cells to become adherent.

In yet another example, the method comprises incubating and/or maintaining and/or culturing the cells in high cell-density conditions for up to about 10 days.

In one example, the method comprises detaching the cells before incubating the cells in high cell density conditions.

In one example, the method comprises detaching the cells after incubating the cells in high cell density conditions.

In one example, the method further comprises isolating progenitor cells capable of being differentiated into a plurality of different cell types.

In one example, the method further comprises storing progenitor cells capable of being differentiated into a plurality of different cell types.

In one example, there is provided a progenitor cell capable of being differentiated into a plurality of different cell types, wherein said cell is a product of the method according to any one of the examples described herein.

In another example, there is provided an isolated progenitor cell of fibroblast origin, wherein the progenitor cell is capable of being differentiated into a plurality of different cell types.

In one example there is provided a method for producing a differentiated cell comprising incubating a progenitor cell according to any example herein for a time and under conditions sufficient to produce a differentiated cell.

According to one example, the method comprises incubating the progenitor cell in vitro.

In another example, the method comprises incubating the progenitor cell in vivo.

In on example, the method further comprises isolating the differentiated cell.

In one example, the method further comprises storing the differentiated cell.

In one example, there is provided a differentiated cell, wherein said cell is a product of the method according to any example described herein.

In another example, there is provided a cell culture comprising a plurality of progenitor cells and/or differentiated cells derived therefrom produced according to any example described herein.

In one example, there is provided a method for producing and/or repairing and/or regenerating a tissue or an organ comprising incubating a progenitor cell, a differentiated cell or a cell culture according to any example described herein for a time and under conditions sufficient to produce and/or repair and/or regenerate one or more tissues or organs from the cell or cell culture.

According to one example the method comprises culturing or perfusing the cells or cell culture onto or into a biocompatible scaffold or matrix for a time and under conditions sufficient for the cell or cell culture to produce and/or repair and/or regenerate one or more tissues or organs.

In one example, the scaffold or matrix comprises non-cellular polymer.

In another example, the non-cellular polymer comprises a synthetic compound.

In yet another example, the scaffold or matrix comprises a decellularized tissue or organ or a derivative thereof.

In yet another example, the scaffold or matrix comprises collagen and/or proteoglycan.

In one example, the method further comprises incubating the progenitor cell, differentiated cell or cell culture in the presence of at least one growth factor or mitogen or functional fragment thereof or nucleic acid encoding said growth factor, mitogen or functional fragment.

In one example, the method further comprises isolating the tissue(s) or organ(s) and optionally, providing the tissue(s) or organ(s) to a subject in need thereof.

In one example, there is provided an isolated tissue or organ produced, repaired or regenerated by the method according to any example described herein.

In another example, there is provided a pharmaceutical composition comprising a progenitor cell, differentiated cell or cell culture according to any example described herein and a pharmaceutically acceptable carrier.

In another example, there is provided a method of prophylaxis or treatment of a condition requiring organ or tissue formation and/or regeneration and/or repair in a subject, said method comprising administering or transplanting or grafting to said subject an effective amount of the progenitor cell, differentiated cell, cell culture, tissue or organ according to any example described herein, thereby preventing or treating the condition in the subject.

In yet another example, there is provided a method of prophylaxis or treatment of a condition in a subject that is normally alleviated by administering, grafting or transplanting stem cells or a tissue or organ to a subject, said method comprising administering or transplanting or grafting to said subject an effective amount of the progenitor cell, differentiated cell, cell culture, tissue or organ according to any example described herein, thereby preventing or treating the condition in the subject.

In one example, the present invention provides a progenitor cell, differentiated cell, cell culture, tissue or organ according to any example described herein for use as a medicament.

In another example, the present invention provides a progenitor cell, differentiated cell, cell culture, tissue or organ according to any example described herein for use as a medicament to stimulate or enhance tissue or organ formation and/or regeneration and/or repair.

In another example, the present invention provides a progenitor cell, differentiated cell, cell culture, tissue or organ according to any example described herein for use as a medicament in the treatment or prophylaxis of one or more conditions normally alleviated by administering stem cells or tissue or organ derived from stem cells to a subject or by grafting stem cells or tissue or organ derived from stem cells into a subject or by transplanting stem cells or tissue or organ derived from stem cells into a subject.

In yet another example, the present invention provides use of a progenitor cell, differentiated cell, cell culture, tissue or organ according to any example described herein in the preparation of a medicament for stimulating or enhancing tissue or organ formation and/or regeneration and/or repair in a subject.

In yet another example, the present invention provides a composition comprising a progenitor cell, differentiated cell, cell culture, tissue or organ according to any example described herein and a biocompatible scaffold or matrix.

In yet another example, the present invention provides a kit for regenerating and/or repairing and/or building a tissue or an organ, wherein said kit comprises:
 (i) a progenitor cell, differentiated cell or cell culture according to any example described herein; and (ii) a biocompatible scaffold or matrix;

(iii) optionally, at least one growth factor or mitogen or functional fragment thereof or nucleic acid encoding said growth factor, mitogen or functional fragment; and (iv) optionally, directions for preparing, maintaining and/or using the cells or the scaffold material or matrix including any cell culture or tissue or organ derived therefrom.

In another example, the present invention provides a method for producing a progenitor cell capable of being differentiated into a plurality of different cell types, said method comprising incubating differentiated cells with an amount of an agonist or partial agonist of the Akt/(PKB) pathway and/or NF-kB pathway for time and under conditions sufficient to render the cells capable of being differentiated into a plurality of different cell types.

Unless the context requires otherwise or specifically stated to the contrary, integers, steps, or elements of the invention recited herein as singular integers, steps or elements clearly encompass both singular and plural forms of the recited integers, steps or elements.

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each example described herein is to be applied mutatis mutandis to each and every other example unless specifically stated otherwise.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific examples described herein, which are intended for the purpose of exemplification only. Functionally-equivalent products, compositions and methods are clearly within the scope of the invention, as described herein.

The present invention is performed without undue experimentation using, unless otherwise indicated, conventional techniques of molecular biology, developmental biology, mammalian cell culture, recombinant DNA technology, histochemistry and immunohistochemistry and immunology. Such procedures are described, for example, in the following texts that are incorporated by reference:

1. Sambrook, Fritsch & Maniatis, Molecular Cloning: A Laboratory Manual, Cold Spring Harbor Laboratories, New York, Second Edition (1989), whole of Vols I, II, and III;
2. DNA Cloning: A Practical Approach, Vols. I and II (D. N. Glover, ed., 1985), IRL Press, Oxford, whole of text;
3. Oligonucleotide Synthesis: A Practical Approach (M. J. Gait, ed., 1984) IRL Press, Oxford, whole of text, and particularly the papers therein by Gait, pp1 22; Atkinson et al., pp 35-81; Sproat et al., pp 83-115; and Wu et al., pp 135-151;
4. Nucleic Acid Hybridization: A Practical Approach (B. D. Hames & S. J. Higgins, eds., 1985) IRL Press, Oxford, whole of text;
5. Animal Cell Culture: Practical Approach, Third Edition (John R. W. Masters, ed., 2000), ISBN 0199637970, whole of text;
6. Methods In Enzymology (S. Colowick and N. Kaplan, eds., Academic Press, Inc.), whole of series;

DETAILED DESCRIPTION OF THE PREFERRED EMBODIMENTS

1. Cell Types—Starting Material

The present invention contemplates that any differentiated animal cell type including terminally differentiated animal cells may be used as starting cells for the method of the invention. For example, the starting cells are primary cells, a cell strain, or a cell line.

By "differentiated cell type" is meant a differentiated animal cell type that expresses defined specialized properties that are characteristic of that cell type. These defined specialized properties are passed onto daughter cells if the differentiated cell type undergoes cellular division. The differentiated cell type may be a cell type that is not actively proliferating. Methods for determining the expressed specialized properties will be apparent to the skilled artisan and/or described herein.

Preferably, the starting cells are readily available in substantial quantities. The starting cells may be derived from any animal and preferably from a mature adult animal. The type of animal preferably includes but is not limited to humans, and includes any animal species such as: other primate such as ape, chimpanzee, gorilla, monkey, or orang-utan, horse, cow, goat, sheep, pig, dog, cat, bird, fish, rabbit, rodent, such as a mouse or rat.

The present invention also contemplates that the starting cells may be expanded in cell culture prior to use. Methods for expanding the starting cells in culture will be apparent to the skilled artisan and/or described herein.

1.1 Primary Cell Cultures, Cell Strains, and Cell-Lines

Methods for obtaining primary cultures of differentiated starting cells and others are well known in the art, and usually include obtaining the tissue from a biopsy, amputated limb, secretion, excretion, or other source. The tissue may be derived from any part of the body that is readily available including, but not limited to organs such as skin, bone, gut, pancreas, thymus, spleen, blood, bone marrow, spine, or any nervous tissue.

In a preferred example, the tissue is derived from an adult donor. In a further preferred example the tissue is derived from a patient, since this facilitates autologous transplants and thus reduces the likelihood of adverse immunogenic reactions in the patient. In another preferred example, the tissue is derived from a damaged and/or amputated organ e.g., limb or appendage which is in need of regeneration, repair or replacement in the patient.

The tissue sample comprising the desired differentiated starting cells may also contain connective tissue, for example a skin biopsy. As a non-limiting example, in order to isolate human dermal fibroblasts derived from a mammal, preferably a human, a skin biopsy is obtained which is then minced or otherwise cut into smaller pieces or treated to release the differentiated cell. For instance, and without limiting the invention to any particular method of obtaining a cell to be used in the methods described herein, the tissue is often treated with a collagenase or other protease in order to disassociate the cells from the tissue aggregate. These cells are then placed in a tissue culture flask, or dish, along with a nutrient tissue culture media and propagated at a suitable temperature and a suitable $CO_2$ saturation. The suitable temperature is often from about 35° C. to about 37° C., and the suitable $CO_2$ saturation is often about 5-10% in air.

Optionally, the tissue sample may also be a suspension comprising cells, or comprising a liquid such as a blood sample, or an aspirate such as fluid obtained from the spinal column, or from bone marrow. Samples obtained in suspension and/or liquid form are further processed by centrifugation, or separation, and culture techniques. Blood cells and lymphocytes are often obtained from whole blood treated with heparin or another anti-coagulant. The blood is centrifuged on a gradient, such as a Ficoll gradient, and the lymphocytes and other blood cells form a distinct layer often referred to as the "buffy coat". Primary lymphocytes procured by this method can be further separated by their adherence to glass or plastic (monocytes and macrophages adhere, other lymphocytes, in general, do not adhere). Methods for obtaining and culturing both solid tissue and blood cells from a human are well known in the art and are described in, for example, Freshney (2000, Culture of Animal Cells: A Manual of Basic Techniques, 4th Edition, Wiley-Liss, New York, N.Y.).

As a further non-limiting example, peripheral nerve tissue can be obtained using surgical procedures such as nerve biopsies, amputated limbs, and from organ donors and by any other methods well known in the art or to be developed. Potential sources of peripheral nerve include the sciatic nerve, cauda equina, sural nerve of the ankle, the saphenous nerve, the sciatic nerve, or the brachial or antebrachial nerve of the upper limb.

A preferred amount for the starting nerve tissue is between about 10 milligrams to about 10 grams, preferably between about 100 milligrams to about 1-2 gram. Primary human Schwann cells can be isolated and cultured using the methods detailed elsewhere in this invention or methods known in the art. Other methods for the isolation and culture of Schwann cells and other neural cells are well known in the art, and can readily be employed by the skilled artisan, including methods to be developed in the future. The present invention is in no way limited to these or any other methods, of obtaining a cell of interest.

The skilled artisan would appreciate, based upon the disclosure provided herein, that the particular method for obtaining a differentiated starting cell of interest is not limited in any way, but encompasses methods for isolating a cell of interest well known in the art or to be developed in the future.

Preferably, the differentiated starting cells employed in the present invention include, but are not limited to skin cells, epidermal cells, such as, fibroblasts, keratinocytes, and melanocytes, and, epithelial cells, and the like, and neural cells such as those derived from the peripheral nervous system (PNS) and central nervous system (CNS) including, but not limited to, glial cells, such as, e.g., Schwann cells, astrocytes, oligodendrocytes, microglial cells, and blood cells, such as lymphocytes, including T cells and B cells, macrophages, monocytes, dendritic cells, Lagerhans cells, eosinophils, and the like, adipocytes, cardiac muscle cells, cardiac fibroblasts, osteoclasts, osteoblasts, endocrine cells, β-islet cells of the pancreas, endothelial cells, epithelial cells, granulocytes, hair cells, mast cells, myoblasts, Sertoli cells, striated muscle cells, zymogenic cells, oxynitic cells, brush-border cells, goblet cells, hepatocytes, Kupffer cells, stratified squamous cells, pneumocytes, parietal cells, podocytes, synovial cells, such as synovial fibroblasts, serosal cells, pericytes, chondrocytes, osteocytes, Purkinje fiber cells, myoepithelial cells, megakaryocytes, and the like.

The present invention further includes starting cells of primary cells from any of the aforementioned sources that may be purchased from any commercial source including PromoCell® (Banksia Scientific Company, QLD).

The present invention further includes starting cells of primary cells obtained from or present in the human or animal body.

The present invention further includes starting cells of primary strains or cells lines established in culture, or to be established in culture in the future that may be purchased from any commercial source including American Type Culture Collection (Rockville, Md.).

By "primary strain" shall be taken to indicate any cell type derived as described by any example herein that is established in culture, and that expresses defined specialized properties that are passed onto daughter cells during cellular division, and have a limited life span in culture. Methods for determining the expressed specialized properties will be apparent to the skilled artisan and/or described herein.

By "cell line" shall be taken to indicate any cell type derived as described by any example herein that is established in culture, and that expresses defined specialized properties that are passed onto daughter cells during cellular division, and have an indefinite life span in culture. Methods for determining the expressed specialized properties will be apparent to the skilled artisan and/or described herein.

Preferably, the primary strain, or cell line used as starting material has specialized properties that define the cell type, and such defined cell types include, but are not limited to: skin cells, epidermal cells, such as, fibroblasts, keratinocytes, and melanocytes, and, epithelial cells, and the like, and neural cells such as those derived from the peripheral nervous system (PNS) and central nervous system (CNS) including, but not limited to, glial cells, such as, e.g., Schwann cells, astrocytes, oligodendrocytes, microglial cells, and blood cells, such as lymphocytes, including T cells and B cells, macrophages, monocytes, dendritic cells, Lagerhans cells, eosinophils, and the like, adipocytes, cardiac muscle cells, cardiac fibroblasts, cardiomyocytes, osteoclasts, osteoblasts, endocrine cells, β-islet cells of the pancreas, endothelial cells, epithelial cells, granulocytes, hair cells, mast cells, myoblasts, Sertoli cells, striated muscle cells, zymogenic cells, oxynitic cells, brush-border cells, goblet cells, hepatocytes, Kupffer cells, stratified squamous cells, pneumocytes, parietal cells, podocytes, synovial cells, such as synovial fibroblasts, serosal cells, pericytes, chondrocytes, osteocytes, Purkinje fiber cells, myoepithelial cells, megakaryocytes, and the like.

In one example the present invention utilizes a starter cell that is not sensitive to low-serum culture conditions. Such a starter cell is not sensitive to culturing in low serum for the period the cell is required to be maintained in low serum conditions.

By "starter cell" is taken to mean any differentiated primary cell, cell strain, or cell line as derived and/or obtained by any example described herein.

By "not sensitive to low-serum culture conditions" is taken to mean does not undergo cell death and/or has activated one or more pro-survival pathway(s). For example, cell death is the result of the induction or outcome of any cellular process that includes but is not limited to necrosis, apoptosis or programmed cell death.

By "pro-survival pathway" is taken to mean any pathway that overcomes the induction of one or more cellular processes that result in cell death.

In another example, the present invention utilizes a starter cell that is not sensitive to low-serum culture conditions, and that is induced in one or more pro-survival pathway(s) such that the incubation time in low-serum can be reduced. The present invention contemplates the induction of any cellular pro-survival pathway known in the art, or that may become known in the future such that it may be induced to reduce the culture time in low serum.

In another example, the present invention utilizes a starter cell that is sensitive to low-serum culture conditions, and induced in one or more pro-survival pathway(s) such that the incubation time in low-serum can be reduced. The present invention contemplates the induction of any cellular pro-survival pathway known in the art, or that may become known in the future such that it may be induced to reduce the culture time in low serum.

By "sensitive to low-serum culture conditions" is taken to mean undergoes cell death and/or has not activated one or more pro-survival pathway(s). For example, cell death is the result of the induction or outcome of any cellular process that includes but is not limited to necrosis, apoptosis or programmed cell death.

In one example, the culture time in low-serum as described in any example herein is reduced by any time less than 7 days by activating the Akt/(PKB) pathway, also referred to as protein kinase B (PKB).

In another example, the culture time in low-serum as described in any example herein is reduced by activating the NF-κB pathway.

In one example the present invention utilizes a starter cell that is not sensitive to high cell density culture conditions used by the method of the invention. Such a starter cell is not sensitive to incubation of cells at a starting density of detached cells of about 1500 cells/mm$^2$ plating surface area to about 200,000 cells/mm$^2$ plating surface area or greater, including about 1,850 cells/mm$^2$ surface area of the culture vessel or greater, or about 2,220 cells/mm$^2$ surface area of the culture vessel or greater, or about 2,590 cells/mm$^2$ surface area of the culture vessel or greater, or about 2,960 cells/mm$^2$ surface area of the culture vessel or greater, or about 2,220 cells/mm$^2$ surface area of the culture vessel or greater, or about 3,330 cells/mm$^2$ surface area of the culture vessel or greater, or about 3,703 cells/mm$^2$ surface area of the culture vessel surface area of the culture vessel or greater, or about 7,407 cells/mm$^2$ surface area of the culture vessel surface area of the culture vessel or greater.

By "not sensitive to high cell density culture conditions" is taken to mean does not undergo cell death and/or has activated one or more pro-survival pathway(s). For example, cell death is the result of the induction or outcome of any cellular process that includes but is not limited to necrosis, apoptosis or programmed cell death.

In another example, the present invention utilizes a starter cell that is not sensitive to high cell density culture conditions, and that is induced in one or more pro-survival pathway(s) such that the incubation at high cell density condition does not affect survival of the cell. The present invention contemplates the induction of any cellular pro-survival pathway known in the art, or that may become known in the future such that it may be induced to survival of the cell under high cell density conditions.

In another example, the present invention utilizes a starter cell that is sensitive to high cell density culture conditions, and induced in one or more pro-survival pathway(s) such that the incubation time in high cell density conditions can be reduced and/or the survival of the cell in high density conditions is enhanced. The present invention contemplates the induction of any cellular pro-survival pathway known in the art, or that may become known in the future such that it may be induced to reduce the culture time in high cell density culture conditions, and/or enhance survival of the cell under such conditions.

By "sensitive to high density culture conditions" is taken to mean undergoes cell death and/or has not activated one or more pro-survival pathway(s). For example, cell death is the result of the induction or outcome of any cellular process that includes but is not limited to necrosis, apoptosis or programmed cell death.

In one example, survival of the cells in high density culture conditions as described in any example herein is enhanced by activating the Akt/(PKB) pathway, also referred to as protein kinase B (PKB).

In another example, survival of the cells in high density culture conditions as described in any example herein is enhanced by activating the NF-κB pathway.

1.2. Induction of the Akt/(PKB) Pathway

The method to induce the Akt/(PKB) pathway in a starter cell may comprise contacting the starter cell with any one or more factors that induce(s) the Akt/(PKB) signaling pathway. For example, an inducer initiates and/or enhances Akt/(PKB) pathway signaling in a starter cell. Such an inducer is also referred to as an Akt/(PKB) pathway enhancer or an Akt/(PKB) pathway agonist. For example, the inducer is a peptide, a polypeptide, a chemical, a nucleic acid, an antibody, an antibody fragment or a small molecule, or any insult that induces cellular stress such as, but not limited to, hypoxia, or UV irradiation.

The present invention contemplates any inducer of the Akt/(PKB) signaling known in the art or to be developed in the future. Preferably, the inducer of Akt/(PKB) signaling includes, but is not limited to factors such as: platelet derived growth factor (PGDF-BB), insulin growth factor (IGF-1), transforming growth factor-beta (TGF-β), nerve growth factor (NGF) and carbachol, pyruvate, cytokines such as IL-1, or any active fragment or active chemical group thereof. A method for inducing the Akt/(PKB) pathway with PDGF-BB includes as described in Li et al., Mol. Biol. Cell 15:294-309 (2004) or Gao et al, J. Biol. Chem. 280:9375-9389 (2005) or any references as described therein. A method for inducing the Akt/(PKB) pathway by co-activation with carbachol and NGF includes as described in Wu and Wong Cellular Signalling 18:285-293 (2006) or any references as described therein. A method for inducing the Akt/(PKB) pathway with IGF-1 includes as described in Kulik and Weber Mol. Cell. Biol. 18:6711-6718 (1998) or any reference as described therein. A method for the induction of the Akt/(PKB) pathway by TGF-β includes as described in by Conery et al., Nat Cell Biol (2004) 6: 366-72 or as described by Horowitz et al., J. Biol. Chem. 279: 1359-1367 (2004) or any reference as described therein. Other methods for inducing the Akt/(PKB) pathway with these factors includes methods as described in any one of the Examples or as described in Song et al., J. Cell. Mol. Med. 9:59-7 (2005); Dillon et al., Oncogene 26:1338-1345 or any reference as described therein.

In another preferred example, the inducer of Akt/(PKB) signaling includes activating a receptor that initiates and/or enhances the Akt/(PKB) signaling pathway by contacting the receptor of a starter cell with a peptide, a polypeptide, a chemical, a nucleic acid, an antibody, an antibody fragment or a small molecule, such that the receptor activation initiates and/or enhances the Akt/(PKB) signaling pathway.

Preferably, the receptor is a growth factor receptor such as IGF receptor tyrosine kinase, or the TGF-β type I serine/threonine kinase receptor, or the TGF-β type II serine/threonine kinase receptor, or TGF-β type III receptor, or any one of the integrin receptors, such as α2β1 α1β1, and αv 3, or a GPCR receptor, or a cytokine receptor such as the IL-1 receptor, or a B-cell receptor.

In another preferred example, the inducer of Akt/(PKB) signaling includes activating any intracellular signalling intermediate that initiates and/or enhances the Akt/(PKB) signaling pathway by contacting a starter cell with a peptide, a polypeptide, a chemical, a nucleic acid, an antibody, an antibody fragment or a small molecule, such that the activation initiates and/or enhances the Akt/(PKB) signaling pathway. These intracellular intermediates include but are not limited to downstream signalling intermediates activated by growth factor receptors such as, GAB1, GAB2, IRS1, PI3K, PIP2, PIP3, ras, or downstream signalling intermediates activated by integrin receptors such as, FAK, paxillin, ILK, PI3K, PIP2, PIP3, or downstream signalling intermediates activated by cytokine receptors, such as, JAK1, PI3K, PIP3, PDK-1 or downstream signalling intermediates activated by B-cell receptors such as, BCAP, PI3K, PDK-1, downstream signalling intermediates activated by GPCR receptors such as, GβGγ/PI3K, PIP3, PDK-1.

A method to measure the activation of the Akt/(PKB) pathway includes any method that measures the activity of Akt/(PKB), or any known intracellular signaling intermediate of the Akt/(PKB), as described in Kulik and Weber Mol. Cell. Biol. 18:6711-6718 (1998), or any reference described therein. For example, the phosphorylation of Akt/(PKB) may be used as a marker of the activation of the pathway. The method to measure Akt/(PKB) phosphorylation is described in Kulik and Weber. Briefly, after incubation with factors to induce the Akt/(PKB) pathway, cells are placed on ice and lysed in 1% Nonidet P-40, 0.5% deoxycholate, 150 mM NaCl, and 20 mM HEPES supplemented with phosphatase and protease inhibitors. Insoluble material is pelleted by centrifugation at 10,000×g for 20 min, and the supernatants are equalized for protein concentration by the addition of NLB. Samples are subjected to Western Blot analysis by standard methods using a phospho-Akt (S473) specific antibody. The membrane is stripped and reprobed with Akt-specific antibodies.

In yet another example, an agonist or partial agonist of the Akt/(PKB) pathway is a compound that is not known to exhibit agonism or partial agonism and/or does not exhibit agonism or partial agonism towards a protein kinase C (PKC) enzyme e.g., a phorbol ester.

In yet another example, an agonist or partial agonist of the Akt/(PKB) pathway is a compound that activates one or more components of the Akt/(PKB) pathway i.e., it does not merely de-repress the Akt/(PKB) pathway e.g., by preventing or down-regulating inhibition or antagonism or inverse agonism of the Akt/(PKB) pathway or a pathway component.

1.3. Induction of the NF-κB Pathway

The method to induce the NF-κB pathway in a starter cell may comprise contacting the starter cell with any one or more factors that induce(s) the NF-κB signaling pathway in said primary cell, cell strain or cell line. For example, an inducer initiates and/or enhances NF-κB pathway signaling in a starter cell. Such an inducer is also referred to as an NF-κB pathway enhancer or an NF-κB pathway agonist.

The present invention contemplates any inducer of NF-κB signaling known in the art or to be developed in the future. For example, the inducer is a peptide, a polypeptide, a chemical, a nucleic acid, an antibody, an antibody fragment or a small molecule, or any insult that induces cellular stress such as, but not limited to, hypoxia, UV irradiation, or high cell density.

Preferably, the inducer of NF-κB signaling includes, but is not limited to factors such as: tumor necrosis factor-alpha (TNF-α), interleukin 1 (IL-1), or any active fragment thereof, lysophosphatidic acid (LPA), pyruvate, or lipopolysaccharide (LPS). A method for inducing the NF-κB signaling pathway with TNF-α includes as described in Kouba et al., J. Biol. Chem. 276:6214-6244 (2001) or any reference as described therein. A method for inducing the NF-κB signaling pathway with IL-1 includes as described in Kessler et al., J. Exp. Med. 176:787-792 (1992) or any reference as described therein. A method for inducing the NF-κB signaling pathway with LPA includes as described in Shahrestanifar et al., J. Biol. Chem. 274:3828-3833 (1999) or any reference as described therein. Other methods for inducing the NF-κB signaling pathway with any of these factors includes as described in any one of the Examples.

In another preferred example, the inducer of NF-κB signaling includes activating a receptor that initiates and/or enhances the NF-κB signaling pathway by contacting the receptor of a starter cell with a peptide, a polypeptide, a chemical, a nucleic acid, an antibody, an antibody fragment or a small molecule, or any insult that induces cellular stress such as UV irradiation or incubating cells at high cell density, such that the receptor activation initiates and/or enhances the NF-κB signaling pathway.

Preferably, the inducer of NF-κB signaling comprises incubating differentiated cells at high cell density conditions.

Preferably, the receptor is a cytokine receptor such as the IL-1 receptor, or the TNF receptor, or a growth factor receptor such as, the IGF receptor, or the LPS receptor, such as TLRs, or the T-cell receptor, or the B-cell receptor.

In another preferred example, the inducer of NF-κB signaling includes activating any intracellular signalling intermediate that initiates and/or enhances the NF-κB signaling pathway by contacting a starter cell with a peptide, a polypeptide, a chemical, a nucleic acid, an antibody, an antibody fragment or a small molecule, such that the activation initiates and/or enhances the NF-κB signaling pathway. These intracellular intermediates include but are not limited to downstream signalling intermediates activated by growth factor receptors, such as, PI3K, Akt/PKB, or by the TNF receptor(s) such as TRADD/RIP/FADD/TRAF, NIK/MEKK, or the cytokine receptors, such as TRAF6/MyoD/IRAK, IRAK/TRAF6, TAK1 or T-cell receptors such as, Vav/PKC/ZAP70, BIMP/BCL10/MALT or B-cell receptors such as, BLK/Lyn/Fyn, PKC, BIMP/BCL10/MALT.

A method to measure the activation of the NF-κB pathway includes any method that measures the activity of NF-κB, such as the translocation of NF-κB. Such methods are well known in the art and includes methods as described in Ding et al., J Biol Chem, 273:28897-28905 (1998) or any reference as described therein. Briefly, cells that have been induced in their NF-κB pathway are fixed with 4% formaldehyde in phosphate-buffered saline for 20 min at room temperature, permeabilized with 0.1% Triton X-100 in phosphate-buffered saline for 5 min at room temperature, and then washed twice with 0.1 M Tris-HCl buffer, pH 7.8. To block nonspecific antigenic sites, cells are incubated for 20 min with 5% non-fat dry milk in 0.1M phosphate buffer, pH 7.8, at room temperature. Cells are washed two times in 0.1M Tris wash buffer, incubated for 1 h with rabbit anti-p65 NF-κB antibody (Santa Cruz Biotechnology, Inc., Santa Cruz, Calif.) diluted 1:2000 in 0.1M phosphate buffer, pH 7.8, with 0.1% bovine serum albumin (fraction V; Sigma). The plates are washed three times in Tris wash buffer and incubated 30 min, room temperature, with a 10 μg/ml solution in water of biotinylated anti-rabbit IgG (Vector Laboratories, Burlingame, Calif.). The plates are washed three times in Tris wash buffer and incubated 30 min, room temperature, with 2.5 μg/ml solution of Texas Red avidin (Vector) in the phosphate/bovine serum albumin buffer. The cells are washed three times in Tris wash buffer and stored in 0.1M Tris. Two hours prior to analysis a 1 μg/ml solution of Hoechst 33342 (Molecular Probes, Inc., Eugene, Oreg.) in phosphate-buffered saline is added to each well at room temperature, and the wells are scanned and analysed in the ArrayScan™ cytometer (Cellomics, Inc., Pittsburgh, Pa.).

In yet another example, an agonist or partial agonist of the NF-κB pathway is a compound that is not known to and/or does not exhibit agonism or partial agonism towards a protein kinase C (PKC) enzyme e.g., a phorbol ester.

In yet another example, an agonist or partial agonist of the NF-κB pathway is a compound that activates one or more components of the NF-κB pathway i.e., it does not merely de-repress the NF-κB pathway e.g., by preventing or down-regulating inhibition or antagonism or inverse agonism of the NF-κB pathway or a pathway component.

2. Detachment of Adherent Cells in Culture

In accordance with the generality of the invention, the means by which adherent cells in culture are detached from each other and/or from the culture vessel may be varied.

In a preferred example, adherent cultures are detached from tissue culture plates by incubation of the adherent cells in trypsin for a time and under conditions sufficient for detachment to occur e.g., as described in the Examples.

Trypsin may be purchased from a variety of commercial sources in stock concentrations up to about 2.5% (w/v) trypsin, such as, for example, from GIBCO (Invitrogen). The final trypsin concentration used to achieve detachment when using such a solution is preferably about 0.01% (w/v) to about 0.25% (w/v) trypsin, including about 0.05% (w/v), or about 0.10% (w/v), or about 0.11% (w/v), or about 0.12% (w/v), or about 0.13% (w/v), or about 0.14% (w/v), or about 0.15% (w/v), or about 0.16% (w/v), or about 0.17% (v/v) or about 0.18% (w/v) or about 0.19% (w/v) or about 0.2% (w/v) or about 0.25% (w/v).

It will be apparent to the skilled artisan that the time of incubation in trypsin solution may vary according to cell type, and it is well within the ken of a skilled addressee to determine such parameters without undue experimentation. For example, the time of incubation in trypsin solution is sufficient for the cells to lift from the plates and/or preferably, to detach from each other as determined by the degree of cell clumping or aggregation.

It will also be apparent to the skilled artisan that the temperature for the incubation in trypsin solution is preferably between about 15° C. and about 37° C., or preferably room temperature, or more preferably 37° C. By "room temperature" is meant ambient temperature e.g., between about 18° C. and about 25° C.

Other suitable methods for achieving detachment of cells from each other and/or from the culture vessel include, but are not limited to, cold shock; treatments to release integrin receptors from the extracellular matrix, which comprises fibronectin, vitronectin, and one or more collagens; activation of degradation of matrix molecules including, but not limited to fibronectin, collagens, proteoglycans, and thrombospondin; inducing or enhancing the secretion of proteases, such as, but not limited to collagenase, stromelysin, matrix-metalloproteinases (MMPs; a class of structurally related zinc-dependent endopeptidases that collectively degrade extracellular matrix components) or plasminogen activator; and decreasing or repressing the expression of protease inhibitors, plasminogen activator inhibitor (PAI-1) or tissue inhibitors of metalloproteinases (TIMPs). Such methods are described without limitation for example, by Ivaska and Heino, Cell. Mol. Life. Sci. 57:16-24 (2000), Nagase et al., Cardovasc. Res. 69(3):562-73 (2006) or a reference cited therein. Preferred cold shock means comprise incubating the cells in ice-cold phosphate buffered saline (PBS) or other isotonic buffer for a time and under conditions sufficient for detachment to occur. Preferred conditions include cold shock for about 10 minutes or until the cells lift from the plates and/or detach from each other as determined by the degree of cell aggregation.

A further means for achieving detachment of cells from each other and/or from the culture vessel includes incubating the cells in a citric saline (e.g., 0.135M potassium chloride, 0.015M sodium citrate). Preferred citric saline treatment comprises incubating the cells and citric saline in PBS at 37° C. and decanting cells for a time and under conditions sufficient for cells to lift from the plates and/or detach from each other as determined by the degree of cell aggregation.

Integrin receptors can be released from the extracellular matrix by incubating the cells with a synthetic peptide comprising the Arg-Gly-Asp sequence that competes for binding to the integrin receptors such as described, for example, by Haymen et al., Journal Cell Biol, 100:1948-1954 (1985). Alternatively, or in addition, integrin receptors are released from extracellular matrix by incubating cells in a $Ca^{2+}$-free and Me-free solution comprising EDTA (e.g., $Ca^{2+}$-free and $Mg^+$-free PBS comprising EDTA, or other $Ca^{2+}$-free and $Mg^+$-free isotonic buffer) essentially as described by Sambrook, Fritsch & Maniatis, Molecular Cloning: A Laboratory Manual, Cold Spring Harbor Laboratories, New York, Second Edition (1989), whole of Vols I, II, and III; Animal Cell Culture: Practical Approach, Third Edition (John R. W. Masters, ed., 2000), ISBN 0199637970, whole of text; Methods In Enzymology (S. Colowick and N. Kaplan, eds., Academic Press, Inc.), whole of series.

Preferred means for inducing or enhancing MMP expression include induction by addition of growth factor or cytokine to the culture medium.

The present invention clearly encompasses the use of any means by which adherent cells in culture are detached from each other and/or from the culture vessel as described by Ivaska and Heino, Cell. Mol. Life. Sci. 57:16-24 (2000) and references described therein.

3. Ligands of Protease Activated Receptors (PARS)

In an alternative example, adherent cultures are detached from tissue culture plates by incubation of the adherent cells in the presence of one or more PAR ligands for a time and under conditions sufficient for detachment to occur e.g., as described in the Examples.

By "protease-activated receptor" or "PAR" is meant any one of a class of G-protein coupled receptors including, but not limited to, the receptors designated PAR1, PAR2, PAR3, and PAR4, and combinations thereof.

Activation of a PAR by its cognate endogenous or non-endogenous ligand leads to a cascade of cellular events such as, for example, contraction of myometrium and/or vascular and/or smooth muscle and/or activation of mitogen-activated protein kinases as described e.g., by Shintani et al., British Journal of Pharmacology (2001) 133, 1276-1285 or Belham et al., Biochem J. 320: 939-946, 1996. Alternatively, or in addition, activation of PAR by the ligand may protect cells from apoptosis and/or activate the Akrt pathway and/or activate the NF-kappaB pathway. Activation of the Akrt pathway and/or activate the NF-kappaB pathway can be determined e.g., by detecting expression of one or more pathway intermediates in cells.

Preferred PAR ligands include, but are not limited to trypsin, tryptase, chymotrypsin, elastase, thrombin, plasmin, coagulation factor Xa, granzyme A and cathepsin G.

PAR ligands that are proteases can be purchased from a variety of commercial sources and used, for example at concentrations in the range of about 0.01% (w/v) to about 0.25% (w/v). It will be apparent to the skilled artisan that the time of incubation in a PAR ligand may vary according to cell type, and it well within the ken of a skilled addressee to determine such parameters without undue experimentation. For example, the time of incubation is sufficient for activation of one or more downstream cellular effects of the receptor to occur, as determined by routine procedures. It will also be apparent to the skilled artisan that the temperature for the incubation in PAR ligand is preferably between about 15° C. and about 37° C., or preferably room temperature, or more preferably 37° C.

For example, Ishii et al., J. Biol. Chem. 270 (27):16435-16440 (1995) describe a method for activating PAR using thrombin. Thrombin may be purchased from a variety of commercial sources, e.g., Sigma, and the final thrombin concentration is preferably in the range of about 10 nM to about 100 nM thrombin, including 10 nM thrombin, or 20 nM thrombin, or 30 nM thrombin, or 40 nM thrombin, or 50 nM thrombin, or 60 nM thrombin, or 70 nM thrombin, or 80 nM thrombin, or 90 nM thrombin, or 100 nM thrombin. Preferably, thrombin is diluted in phosphate-buffered saline optionally comprising about 0.5% (v/v) polyethylene glycol 8000. Preferably, cells are incubated with thrombin at about 25° C. for about 60 min.

In another example, Quinton et al., J. Biol. Chem. 279 (18): 18434-18439 (2004) describe activation of PAR using plasmin.

In other examples, PAR can be activated by any one of the methods described by Shintani et al., British Journal of Pharmacology (2001) 133, 1276-1285 or Wang et al., Biochem. J. 408: 221-230 (2007), or Dery et al., Am. J. Physiol. 274 (Cell Physiol. 43): C1429-1452, incorporated herein by reference.

In another preferred example, to activate any one of the PAR receptors the adherent cells are incubated in the presence of a known GPCR receptor agonist.

4. Storage of Cells

In a preferred example, the cells prepared according to the invention are stored in low-serum conditions until required for differentiation. Alternatively, the cells prepared according to the invention are stored in medium containing serum, e.g., DMEM-HG containing 10% FCS.

Optionally, the cells are stored in low serum conditions at 4° C. for a short time. For example, the cells may be stored on ice for 1 min to 6 hours.

Optionally, the cells are cryogenically frozen in liquid nitrogen. The method used to freeze the cells in optimal freezing media and conditions will be apparent to the skilled artisan and is dependent on the cell type. For example, such methods are commercially available from cell suppliers such as American Type Culture Collection (Rockville, Md.) or PromoCell® (Banksia Scientific Company, QLD). Methods that are used are also described in Animal Cell Culture: Practical Approach, Third Edition (John R. W. Masters, ed., 2000), ISBN 0199637970.

5. Differentiation

The present invention contemplates that the cells prepared according to the invention are differentiated into any other differentiated cell type. For example, a cell type of a tissue that is required for regeneration. The tissue may be a tissue of any part of the body including but not limited to organs such as skin, bone, gut, stomach, pancreas, thymus, thyroid, eye, spleen, heart, blood vessels, cardiovascular, blood, bone marrow, or any nervous tissue.

Preferably, the cells of the invention are differentiated to, but not limited to: skin cells, epidermal cells, keratinocytes, and melanocytes, and, epithelial cells, and the like, and neural cells such as those derived from the peripheral nervous system (PNS) and central nervous system (CNS) including, but not limited to, glial cells, such as, e.g., Schwann cells, astrocytes, oligodendrocytes, microglial cells, and blood cells, such as lymphocytes, including T cells and B cells, macrophages, monocytes, dendritic cells, Lagerhans cells, eosinophils, and the like, adipocytes, cardiomyocytes, cardiac muscle cells, cardiac fibroblasts, osteoclasts, osteoblasts, endocrine cells, n-islet cells of the pancreas, endothelial cells, epithelial cells, granulocytes, hair cells, mast cells, myoblasts, Sertoli cells, striated muscle cells, zymogenic cells, oxynitic cells, brush-border cells, goblet cells, hepatocytes, Kupffer cells, stratified squamous cells, pneumocytes, parietal cells, podocytes, synovial cells, such as synovial fibroblasts, serosal cells, pericytes, chondrocytes, osteocytes, Purkinje fiber cells, myoepithelial cells, megakaryocytes, and the like.

Methods for differentiating cells of the invention include, but are not limited to the methods described in any one of the Examples or an example herein. The present invention also contemplates the differentiation of further cell types including, but not limited to the following.

Neural Tissue Development

To differentiate cells prepared according to the invention, cells that have been de-differentiated according to any example as described herein are then suspended in Neuroblast A medium (Invitrogen/GIBCO) supplemented with 5% horse serum, 1% fetal calf serum, L-glutamine (2 mM), transferrin (100 µg/ml), insulin (2 µg/ml), retinoic acid 0.5 mM, brain-derived neurotrophic factor (10 ng/ml), and then allowed to attach, i.e. are plated onto tissue culture plates in said medium for a time sufficient to differentiate the cells to a neural phenotype.

Dopamine-Secreting Tissue Development

To differentiate cells prepared according to the invention, cells that have been de-differentiated according to any example as described herein are first suspended in dopaminergic induction media (DMEM serum free medium supplemented with 2 mM glutamine, 100 µg/ml streptomycin, 100 U/ml penicillin, 12.5 U/ml nystatin, N2 supplement (Invitrogen, New Haven, Conn.), and 20 ng/ml fibroblast growth factor-2 (FGF-2) and epidermal growth factor (EGF) (both from R&D Systems, Minneapolis, Minn.) for 2-3 days. The medium is then changed to basal induction medium containing Neurobasal and B27 (both from Invitrogen), in addition to 1 mM dibutyryl cyclic AMP (db cAMP), 3-isobutyl-1-methylxanthine (IBMX), and 200 µM ascorbic acid (all from Sigma, St Louis, Mo.) and brain-derived neurotrophic factor (BNDF) 50 ng/ml (Cytolab, Rehovot, Israel), as described in Barzilay et al., Stem cells and Development 17:547-554, 2008 which is herein incorporated by reference. The cells are then allowed to attach, i.e. are plated onto tissue culture plates in said medium for a time sufficient to differentiate the cells to a dopamine secreting phenotype.

Skeletal/Cardiac Muscle Development

To differentiate cells prepared according to the invention, cells that have been de-differentiated according to any example as described herein are then suspended in alpha-Modification of Eagle's Medium supplemented with 10% fetal calf serum, L-glutamine (2 mM), ascorbate-2-phosphate (100 µM/ml), and 5-azacytodine (5 µM/ml) and then allowed to attach, i.e. are plated onto tissue culture plates in said medium for a time sufficient to differentiate the cells to a skeletal/muscle phenotype.

Epithelial Development

To differentiate cells prepared according to the invention, cells that have been de-differentiated according to any example as described herein are then suspended in keratinocyte basal medium (Clonetics) supplemented with Bovine Pituitary Extract (50 µg/ml), epidermal growth factor (10 ng/ml), Hydrocortisone (0.5 µg/ml), Insulin (5 µg/ml) and then allowed to attach, i.e. are plated onto tissue culture plates in said medium for a time sufficient to differentiate the cells to a keratinocyte lineage.

Osteoblasts, Tendon, Ligament or Odontoblast Development

To differentiate cells prepared according to the invention, cells that have been de-differentiated according to any example as described herein are then suspended in alpha-Modification of Eagle's Medium supplemented with 10% fetal calf serum, L-glutamine 2 mM, ascorbate-2-phosphate (100 µM), Dexamethasone ($10^{-7}$M) and BMP-2 (50 ng/ml) and then allowed to attach, i.e. are plated onto tissue culture plates in said medium for a time sufficient to differentiate the cells.

Pericyte or Smooth Muscle Cell Development

To differentiate cells prepared according to the invention, cells are suspended in alpha-Modification of Eagle's Medium supplemented with 10% fetal calf serum, L-glutamine 2 mM, ascorbate-2-phosphate (100 µM), platelet derived growth factor-BB (10 ng/ml) then layered over 200 µl of matrigel in 48-well plates for a time sufficient to differentiate the cells.

Assessment of the Differentiated Phenotype

A method to assess the lineage of differentiated cells of the invention includes, but is not limited to use of commercially available antibodies and flow cytometry. This procedure has been reported previously and is well known in the art. Briefly, differentiated cell cultures are liberated by trypsin/EDTA digest then incubated for 30 min on ice. Approximately $2 \times 10^5$ cells are washed then resuspended in 200 µl of primary antibody cocktail for 1 hr on ice. The primary antibody cocktail consists of saturating concentrations of a mouse IgG monoclonal antibody or rabbit IgG for each tube (Table 1). Antibodies for the markers listed in Table 1 are commercially available from a variety of sources including but not limited to DAKO, Santa Cruz, Pharmingen, or Sigma. For the staining with antibodies reactive with intracellular antigens the cells are first washed with PBS then permeabilized by treatment with 70% ethanol on ice for ten minutes then washed prior to staining. The mouse isotype IgM and IgG negative control Mabs are treated under the same conditions. Following incubation with primary antibodies, cells are washed and exposed to saturating levels of goat anti-mouse IgM µ-chain specific-FITC (1/50 dilution) and either goat anti-mouse IgG γ-specific-PE (1/50 dilution) or anti-rabbit Ig-specific-PE (1/50 dilution) (Southern Biotechnology Associates) in a final volume of 100 µl. The cells are incubated for 45 min on ice, then washed twice then fixed in FAX FIX (PBS supplemented with 1% (v/v), 2% (w/v) D-glucose, 0.01% sodium azide). Flow cytometric analysis is performed using a FACSCalibur flow cytometer and the CellQuest software program (Becton Dickinson Immunocytometry Systems, San Jose, Calif.). Data analysis is performed using CellQuest and the Modfit LT V2.0 software program (Verity Software House, Topsham, Me.).

Table 1: Markers for Lineage Identification
1. Skeletal Muscle: Myo E Desmin
2. Smooth Muscle: SMMHC, SMHC-FAST, alphaS-MAC, PDGF-R, Vimentin;
3. Chondrocytes: Type II Collagen; Collagen IX; Aggrecan; Link Protein; S100; Biglycan;
4. Basal Fibroblasts: Laminin; Type IV Collagen; Versican;
5. Endothelial Cells: vWF; VCAM-1; Endoglin; MUC18; CD31; CD34; SDF-1
6. Cardiomyocytes: Calponin; Troponin I; Troponin C;
7. Neurons: NCAM; GFAP; Neuroanalase; Neurofilament;
8. Bone: AP, Type I Collagen; CBFA 1; OCN; OPG; RANKL; Annexin II
9. Fat: CEPBalpha; PPARgamma; Leptin;
10. Epithelial cells: Keratin 14; Cytokeratin 10+13; EGFR;
11. Fibroblast: Collagen III; NGFR; Fibroblast marker;
12. Haematopoietic: CD14; CD45; Glycophorin-A.

6. Formulations and Treatments

Pharmaceutical compositions and other formulations for application to the human or animal body e.g., for stimulating or enhancing tissue repair in a subject, are suitable for use topically, systemically, or locally as an injectable and/or transplant and/or device, usually by adding necessary buffers.

Preferred formulations for administration, the non-culture expanded cells used in this invention are in a pyrogen-free, physiologically acceptable form.

The cells may be injected in a viscous form for delivery to the site of tissue damage.

Topical administration may be suitable for wound healing and tissue repair.

In one example, therapeutically useful agents may also optionally be included in the progenitor cell formulation, or alternatively, administered simultaneously or sequentially with the composition in the methods of the invention.

In another example, the compositions of the present invention may be used in conjunction with presently available treatments for tendon/ligament injuries, such as suture (e.g., vicryl sutures or surgical gut sutures, Ethicon Inc., Somerville, N.J., USA) or tendon/ligament allograft or autograft, in order to enhance or accelerate the healing potential of the suture or graft.

The choice of a carrier material is based on biocompatibility, biodegradability, mechanical properties, cosmetic appearance and interface properties. The particular application of the progenitor cells will generally define the appropriate carrier. In one example, cells are mixed with a matrix, preferably a biodegradable matrix or a matrix comprised of pure proteins or extracellular matrix components. Other useful matrices include e.g., collagen-based materials including sponges, such as Helistat™ (Integra LifeSciences, Plainsboro, N.J., USA), or collagen in an injectable form, and sequestering agents such as hyalouronic acid-derived materials. Biodegradable materials, such as cellulose films, or surgical meshes, may also serve as matrices. Such matrices may be sutured into an injury site, or wrapped around a site of injury such as a tendon or ligament. Another preferred class of carriers includes polymeric matrices, wherein the progenitor cell of the invention is mixed with a polymer of poly lactic acid, poly glycolic acid, or a copolymer of lactic acid and glycolic acid. These matrices may be in the form of a sponge, or in the form of porous particles, and may also include a sequestering agent. Suitable polymer matrices are described, for example, in WO93/00050.

In another example, the formulations of progenitor cells of the invention may comprise other therapeutically useful agents such as, for example, one or more cytokines, chemokines, leukemia inhibitory factor (LIF/HILDA/DIA), migration inhibition factor, MP52, growth factors including epidermal growth factor (EGF), fibroblast growth factor (FGF), platelet derived growth factor (PDGF), transforming growth factors (TGF-alpha and TGF-beta), and fibroblast growth factor-4 (FGF-4), parathyroid hormone (PTH), insulin-like growth factors (IGF-I and IGF-II), or combinations thereof.

In another example, the formulation comprises at least one other agent that promotes hematopoiesis, such as, for example a cytokine, which participates in hematopiesis. Some non-limiting examples are: CSF-1, G-CSF, GM-CSF, interleukins, interferons, or combinations thereof.

In another example, the formulation comprises at least one other agent that promotes the delivery of systemic proteins such as Factor IX, VIII, growth hormone etc.

In another example, the progenitor cells are genetically engineered to express a protein of interest prior to the application to the subject in need. The protein of interest is any macromolecule, which is necessary for cell growth, morphogenesis, differentiation, tissue building or combinations thereof. These are, for example, a bone morphogenic protein, a bone morphogenic-like protein, an epidermal growth factor, a fibroblast growth factor, a platelet derived growth factor, an insulin like growth factor, a transforming growth factor, a vascular endothelial growth factor, cytokines related to hematopoiesis, factors for systemic delivery as such as GH, factor VIII, factor IX or combinations thereof.

The term "cells engineered to express a protein of interest" is defined hereinabove as a cell or to a tissue which had been modified via molecular biologic techniques, for example via recombinant DNA technology, to express any macromolecule which is necessary for cell growth, morphogenesis, differentiation, tissue building or combinations thereof. In another example, cells are thus modified in order to produce an increased amount of any macromolecule, which is necessary for cell growth, morphogenesis, differentiation, tissue building or combinations thereof.

The step of genetically engineered a cell to express a protein of interest is performed by the transfection or transduction of the cell with a nucleic acid encoding the protein of interest.

The term "transfection" or "transfected cells" refer to cells in which DNA is integrated into the genome by a method of transfection, i.e. by the use of plasmids or liposomes.

The term "transduction" or "transduced cells" refers to viral DNA transfer for example, by phage or retroviruses. The nucleic acid, which encodes the protein of interest, can be introduced by a vector molecule, as well, and represents an additional example of this invention.

The vector molecule can be any molecule capable of being delivered and maintained, within the target cell, or tissue such that the gene encoding the product of interest can be stably expressed. In one example, the vector utilized in the present invention is a viral or retroviral vector or a non-viral DNA plasmid. According to one aspect, the method includes introducing the gene encoding the product into the cell of the mammalian tissue for a therapeutic or prophylactic use. The viral vectors, used in the methods of the present invention, can be selected from the group consisting of (a) a retroviral vector, such as MFG or pLJ; (b) an adeno-associated virus; (c) an adenovirus; and (d) a herpes virus, including but not limited to herpes simplex 1 or herpes simples 2 or (e) lentivirus. Alternatively, a non-viral vector, such as a DNA plasmid vector, can be used. Any DNA plasmid vector known to one of ordinary skill in the art capable of stable maintenance, within the targeted cell, or tissue upon delivery, regardless of the method of delivery utilized is within the scope of the present invention. Non-viral means for introducing the gene encoding for the product into the target cell are also within the scope of the present invention. Such non-viral means can be selected from the group consisting of (a) at least one liposome, (b) $Ca_3(PO_4)_2$, (c) electroporation, (d) DEAE-dextran, and (e) injection of naked DNA.

The term "nucleic acid" refers to polynucleotides or to oligonucleotides such as deoxyribonucleic acid (DNA), and, where appropriate, ribonucleic acid (RNA) or mimetics thereof. The term should also be understood to include, as equivalents, analogs of either RNA or DNA made from nucleotide analogs, and, as applicable to the example being described, single (sense or antisense) and double-stranded polynucleotides. This term includes oligonucleotides composed of naturally occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, enhanced cellular uptake, enhanced affinity for nucleic acid target and increased stability in the presence of nucleases.

The formulations of the invention are useful for treating cartilaginous tissue, defects of the embryonic joint where tendon, ligaments, and bone form simultaneously at contiguous anatomical locations, regenerating tissue at the site of tendon attachment to bone, or for wound healing, such as skin healing and related tissue repair. Types of wounds include, but are not limited to burns, incisions and ulcers.

The formulations of the invention are also useful for tissue renewal or regeneration that ameliorates an adverse condition of tissue, degeneration, depletion or damage such as might be caused by aging, genetic or infectious disease, accident or any other cause, in humans, livestock, domestic animals or any other animal species.

In another example the formulations of the invention are also useful for promoting tissue development in livestock, domestic animals or any other animal species in order to achieve increased growth for commercial or any other purpose.

In another example the formulations of the invention are also useful in plastic surgeries, such as, for example, facial or body reconstruction.

In another example the formulations of the invention are also useful for enhancing repair of tissue injuries, tears, deformities or defects, and for the prophylaxis or prevention of tissue damage.

In another example, the formulations of the invention are also useful for treating and/or preventing osteoporosis, which results from a decrease in estrogen, which may be caused by menopause or ovariectomy in women. Use of the progenitor cells of the present invention for prevention of accelerated bone resorption and inhibition of a decrease of bone volume, bone quality and bone strength is also provided by the invention. Trabecular connectivity and trabecular unconnectivity may be maintained at healthy levels with the pharmaceutical compositions of the present invention. Osteoporosis and its symptoms such as decreased bone volume, bone quality, and bone strength, decreased trabecular connectivity, and increased trabecular unconnectivity may be treated or prevented by administration of a pharmaceutically effective amount of the pharmaceutical composition to a patient in need thereof.

In another example, the formulations of the invention are also useful for regenerating tissues which have been damaged through acute injury, abnormal genetic expression or acquired disease.

In another example, the formulations of the invention are also useful for stimulating skeletal development in livestock, domestic animals or any other animal species in order to achieve increased growth for commercial or any other purpose.

In another example, the formulations of the invention are also useful for treatment of neoplasia or hyperplasia of bone or cartilage or any other tissue, in humans, livestock, domestic animals or any other animal species.

In another example, the formulations of the invention are also useful for stimulating haematopoiesis e.g., in combination with hematopoietic transplants.

The dosage regimen, which is the amount of the cells that are administered in order to obtain a therapeutic effect, is affected by various factors which modify the action of the progenitor cells' composition, e.g., amount of tissue desired to be repaired or formed, the site of injury or damage, the condition of the damaged tissue, the size of a wound, type of damaged tissue, the patient's age, sex, and diet, the severity of any infection, time of administration and other clinical factors. The dosage may vary with the type of matrix used in the reconstitution and the types of additional proteins in the composition. The addition of other known growth factors, such as IGF-I (insulin like growth factor I), to the final composition, may also affect the dosage. Progress can be monitored by periodic assessment of tissue formation and/or growth and/or repair. The progress can be monitored by methods known in the art, for example, X-rays (CT), ultra-sound, MRI, arthroscopy and histomorphometric determinations.

7. Tissue and Organ Building, Repair and Regeneration

The present invention encompasses the use of the progenitor cells prepared according to the invention or differentiated cells derived there from for building, repairing or regenerating a tissue, and/or building, repairing or regenerating an organ. It is apparent that when progenitor cells are used in this example, those progenitor cells differentiate in situ during the tissue/organ building, repair or regeneration, whereas differentiated cells derived from the progenitor cells are not required to differentiate in situ.

It is also apparent that when differentiated cells are employed in this example, multiple cell types may be required to build, regenerate or repair tissues comprising different cell types in nature, or whole organs. One or more, or all, of these different cell types may be produced in accordance with the present invention by employing appropriate differentiation media and conditions. A plurality of progenitor cell populations may each be derived from different starting cells or cell types, or produced in different batches. Similarly, a plurality of differentiated cells may comprise different batches of the same cell type and/or different cell types per se produced from the same or different batches of progenitor cells or the same or different starting cell types.

The organ that is produced, repaired or regenerated is without limitation and includes e.g., skin, bone, gut, stomach, pancreas, thymus, thyroid, eye, spleen, heart, blood vessels, cardiovascular, bone marrow, or nervous system. The tissue may be any tissue without limitation including e.g., a tissue of any one or more of the foregoing organs.

In one example, one or more populations (or batches) of progenitor cells or one or more populations of differentiated cells derived from the progenitor cells as described according to any example hereof is cultured or perfused onto a scaffold or matrix that allows the cells to develop into a tissue or organ or part thereof e.g., a biocompatible scaffold or matrix such as a biodegradable scaffold matrix.

In another example, building or regenerating an organ or multi-layered tissue such as an artificial organ or tissue may be achieved by a process comprising:

(i) perfusing a first population of progenitor cells produced in according with any example hereof or differentiated cells derived therefrom into and/or onto a first side of a biocompatible scaffold or matrix such that the cells attach to the matrix and then culturing the cells for a time and under conditions sufficient to produce a first specialized tissue layer; and (ii) perfusing a second population of undifferentiated or differentiated cells distinct from the cells at (i) into and/or onto a second side of the biocompatible matrix such that the second population of cells attaches to the matrix and then culturing the second population of cells in the matrix for a time and under conditions sufficient to produce a second specialized tissue layer that is different from the first specialized tissue layer
to thereby create a multi-layered tissue and/or organ construct.

This process may be achieved by reversing the order of (i) and (ii).

In another example, building or regenerating an organ or multi-layered tissue such as an artificial organ or tissue may be achieved by a process comprising:
(i) perfusing a first population of progenitor cells produced in according with any example hereof or differentiated cells derived therefrom into and/or onto a first side of a biocompatible scaffold or matrix such that the cells attach to the matrix and then culturing the cells for a time and under conditions sufficient to produce a first specialized tissue layer; and
(ii) perfusing a second population of progenitor cells produced in according with any example hereof or differentiated cells derived therefrom into and/or onto a second side of the biocompatible matrix such that the second population of cells attaches to the matrix and then culturing the second population of cells in the matrix for a time and under conditions sufficient to produce a second specialized tissue layer that is different from the first specialized tissue layer
to thereby create a multi-layered tissue and/or organ construct.

In another example, a multi-layered tissue and/or organ construct can also be created by culturing first and second populations of cells on the same side of the biocompatible matrix.

In another example, different populations of cells are cultured simultaneously or sequentially in and/or on the matrix.

In accordance with these examples, perfused cells are cultured until they differentiate and/or proliferate to produce a first monolayer comprising cells with a desired phenotype and morphology. Once the first monolayer has attained a desired cell density, a second layer of the same cell population is deposited on the first monolayer. The second layer of perfused cells is cultured under conditions to provide nutrients to both the second cell layer and the first monolayer and for time sufficient for cells in the layers to form a bilayer having cells with a desired cell type and morphology. The process is repeated until a poly-layer comprising a plurality of cell monolayers of the desired cell type and morphology is produced. Polylayers may also be produced by layering of multiple bilayers, trilayers, etc.

In another example, the invention provides a tissue construct or organ construct comprising a biocompatible scaffold or matrix perfused with at least one population of progenitor cells of the present invention and/or one or more populations of differentiated cells derived from progenitor cells of the invention. The tissue or organ construct may comprise one or a plurality of cell types or populations or batches e.g., a plurality of cell types on the same or different sides of the biocompatible scaffold or matrix.

As used herein, the term "scaffold" or "matrix" shall be taken to mean any material in and/or on which cells may differentiate and/or proliferate to form a tissue or organ or part thereof. Accordingly, a scaffold or matrix provides the structure or outline to the tissue or organ to be repaired, regenerated or built. A scaffold or matrix will generally be a three-dimensional structure comprising a non-degradable or a biodegradable material, e.g., a decellularized organ or part thereof, that can be shaped into a desired tissue or organ. For example, a scaffold or matrix also provides sufficient interstitial distances required for cell-cell interaction.

As used herein, the term "biocompatible scaffold" or "biocompatible matrix" shall be taken to mean a scaffold or matrix as hereinbefore defined that, with any tissue and/or organ proliferating or growing thereon, is further suitable for implantation into a host subject. When grown in a biocompatible matrix, the proliferating cells mature and segregate properly to form tissues analogous to counterparts found in vivo. In other examples, counter parts tissues or organs present in vivo may be replaced by a tissue and/or organ repaired, regenerated or repaired by the method described herein.

A biocompatible scaffold or matrix is generally a polymeric composition e.g., polyglycolic acid, or the infrastructure of an organ following decellularization i.e., removal of substantially all cellular material. Non-limiting examples of biocompatible polymeric matrixes can be formed from materials selected from the group consisting of, but are not limited to, cellulose ether, cellulose, cellulosic ester, fluorinated polyethylene, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyglycolic acid, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, and copolymers or physical blends thereof. The polymeric matrix can be coated with a biocompatible and biodegradable shaped setting material. In one example, the shape settling material is a liquid copolymer e.g., poly-DL-lactide-co-glycolide. In another example, the scaffold or matrix comprises synthetic or semi-synthetic polymer fibers e.g., Dacron™, Teflon™ or Gore-Tex™.

Preferred non-toxic biocompatible scaffolds or matrices may be made of natural or synthetic polymers, such as, for example, collagen, poly(alpha esters) such as poly(lactate acid), poly(glycolic acid) (PGA), polyorthoesters and polyanhydrides and their copolymers, which degraded by hydrolysis at a controlled rate and are reabsorbed. These materials provide the maximum control of degradability, manageability, size and configuration. Preferred biodegradable polymer material include polyglycolic acid and polygalactin, developed as absorbable synthetic suture material. Polyglycolic acid and polygalactin fibers may be used as supplied by the manufacturer. Other biodegradable materials include cellulose ether, cellulose, cellulosic ester, fluorinated polyethylene, phenolic polymer, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends of these materials.

Decellularized scaffolds or matrices are produced by a process in which the entire cellular and tissue content is removed, leaving behind a complex infra-structure e.g., comprising a fibrous network of stroma or unspecialized connective tissue that predominantly comprises collagen and/or proteoglycan. Decellularized structures can be rigid or semi-rigid. Methods of producing decellularized matrix or scaffold are described e.g., in U.S. Pat. No. 7,354,702 and U.S. Pat. No. 7,429,490, both of which which are incorporated herein by reference.

Scaffolds or matrices may be impregnated with suitable antimicrobial agents and may be colored by a color additive to improve visibility and to aid in surgical procedures.

In one preferred example, the biocompatible polymer is a synthetic absorbable polygalactin material or polyglycolic acid (PGA) fibers (Ethicon Co., Somerville, N.J.; Craig P. H., et al. Surg. 141; 1010 (1975) or Christenson L, et al., Tissue Eng. 3 (1): 71-73; discussion 73-76 (1997)) which can be used as supplied by the manufacturer. This biocompatible polymer may be shaped using methods such as, for example, solvent casting, compression molding, suturing, filament drawing, meshing, leaching, weaving and coating (See Mikos, U.S. Pat. No. 5,514,378, hereby incorporated by reference).

In some examples, the polymers are coated with compounds such as basement membrane components, agar, agarose; gelatin, gum arabic, collagens, such as collagen types I, II, III, IV, and V, fibronectin, laminin, glycosaminoglycans, mixtures thereof, and other hydrophilic and peptide attachment materials having properties similar to biological matrix molecules known to those skilled in the art of cell culture.

Factors, including nutrients, growth factors, inducers of differentiation or dedifferentiation, products of secretion, immunomodulators, inhibitors of inflammation, regression factors, biologically active compounds which enhance or allow ingrowth of the lymphatic network or nerve fibers, and drugs, can be incorporated into the matrix or provided in conjunction with the matrix. Similarly, polymers comprising peptides such as the attachment peptide RGD (Arg-Gly-Asp) can be synthesized for use in forming matrices. Angiogenesis factors, cytokines, extracellular matrix components, and other bioactive materials or drugs may also be impregnated into the scaffold or matrix at any stage preceding implantation e.g., to promote repair, grafting, or reduce or inhibit rejection. Growth factors include e.g., epidermal growth factor (EGF), vascular endothelial growth factor (VEGF), heparin-binding epidermal-like growth factor (HBGF), fibroblast growth factor (FGF), cytokines, genes, proteins, and the like. Other useful additives include antibacterial and antifungal agents to promote healing by suppression of infections. For example, the biocompatible matrix can be fabricated to have a controlled pore structure that allows such nutrients to permeate or contact the perfused cells in the absence of significant cell migration through the pores. In vitro cell attachment and cell viability can be assessed using scanning electron microscopy, histology and quantitative assessment with radioisotopes.

In another example, additional collagenous layers may be added to the inner surfaces of the decellularized structure to create a smooth surface as described in International PCT Publication No. WO 95/22301, the contents of which are incorporated herein by reference. This smooth collagenous layer promotes cell attachment which facilitates growth and development. As described in International PCT Publication No WO 95/22301, this smooth collagenous layer may be made from acid-extracted fibrillar or non-fibrillar collagen, which is predominantly type I collagen, but may also include type II collagen, type IV collagen, or both. The collagen used may be derived from any number of mammalian sources, typically pig and cow skin and tendons. The collagen for example has been processed by acid extraction to result in a fibril dispersion or gel of high purity. Collagen may be acid-extracted from the collagen source using a weak acid, such as acetic, citric, or formic acid. Once extracted into solution, the collagen can be salt-precipitated using NaCl and recovered, using standard techniques such as centrifugation or filtration. Details of acid extracted collagen are described, for example, in U.S. Pat. No. 5,106,949 issued to Kemp et al., incorporated herein by reference.

The present invention will now be illustrated by the following Examples, which are not intended to be limiting in any way. The teachings of all references cited herein are incorporated herein by reference.

EXAMPLE 1

Preparation of Cells Having the Ability to Differentiate into Other Cell Types by Incubation in Low Serum Medium and Treatment with Protease In a first set of experiments for producing cells having the ability to differentiate into different cell types, fibroblasts were cultured different lengths of time in low serum conditions and then either incubated in media without trypsin or comprising trypsin. The cells produced by this method were then tested for their ability to differentiate into adipocytes, as determined by the accumulation of fat. Differentiation into adipocytes was selected in these primary experiments because methods for such differentiation are well-established.

1.1 Materials and Methods
Production of Cells Capable of Differentiating into Other Cell Types Fresh human dermal fibroblasts derived from adult skin or from foreskin were purchased from PromoCell® (Banksia Scientific Company, QLD). Human dermal fibroblasts were plated in cell culture flasks, or plates, in growth medium Dulbecco's Modified Eagle Medium High Glucose (DMEM-HG; e.g., Lonza Cat #12-604) supplemented with 10% FBS (fetal bovine serum), and incubated at 37° C. in a humidified atmosphere of 5% $CO_2$ in air until adherent. Human dermal fibroblasts were plated in two sets, one set of cells were used as control cells, and the second set of cells were used for testing the capability of cells produced by the method to differentiate into adipocytes. Control cells were plated directly onto 96 well plates at about 20,000 cells per well or about 740.74 cells per $mm^2$ surface area. Test cells were plated onto larger plates at the same concentration of cells per well or cells per $mm^2$ surface area. Once all cells were attached, the medium was replaced with medium 199 (e.g., Sigma Cat #2154) supplemented with 0-1% FBS (low-serum) for different periods of time, from 1 to 11 days.

At the conclusion of the incubation period in low serum media, test cells were detached by the addition of 20 μl of detachment solution comprising 0.12% trypsin, 0.02% EDTA and 0.04% glucose (SAFC Biosciences, Cat #59430C) and incubated at 37° C. until cells lifted from the plates. Test cells were recovered from culture, then diluted to 200 μl with medium 199 (e.g., Sigma Cat #2154) and maintained in serum-free medium until required for re-differentiation. Control cells were not detached, and were used directly in the differentiation assay as described below.

Differentiation into Adipocytes

Cells at a density of about 20,000 cells per well or about 740.74 cells per $mm^2$ surface area of the well were incubated in adipogenic medium (Medium 199 comprising 170 nM insulin, 0.5 mM 3-isobutyl-1-methylxanthine, 0.2 mM indomethacin, 1 µM dexamethasone, and 15% rabbit serum) for about 12-21 days. Adipogenic media was replaced every 3 days on both test and control cells.

Assessment of Adipogenesis

After incubation for about 12-21 days in adipogenic medium, the medium was removed, and cells were fixed in 10% formaldehyde solution in aqueous phosphate buffer for at least 1 hour. Cells were then washed with 60% isopropanol and stained with a working solution of Oil Red O solution (in 60% isopropanol, see below for preparation) for 10 minutes. The cells were then washed several times with water, and destained in 100% isopropanol for 15 minutes. The destain solution was removed and the optical density of the solution was measured at 500-510 nm.

The working solution of Oil red O was prepared as previously described (Humason 1972) by dissolving 4.2 g of Oil red O in 1200 ml absolute isopropanol and left overnight without stirring at room temperature. The solution was filtered through analytical filter paper 589-WH (Schleicher and Schuell); after filtration, 900 ml of distilled water was added and the solution was left overnight at 4° C. without stirring and subsequently filtered twice. This working solution was stored at room temperature and had a shelf life of 6-8 months.

1.2 Results

Differentiation potential of control cells compared to test cells at each day post-incubation with low-serum was measured by an assessment of adipogenisis as described above.

Cells that were not incubated in low-serum medium and/or were not incubated in the presence of trypsin did not produce detectable adipocytes. In contrast, fibroblasts that were incubated in low serum medium and then incubated in the presence of trypsin for a time and under conditions sufficient to detach the cells from each other and from the culture plate, were capable of differentiating into adipocytes when cultured in adipogenic medium. Although adipocytes were apparent in cultures incubated from a period of only about 2 days in low-serum, the optimum time for assuming this ability to differentiate e.g., into adipocytes, is about 5-9 days, as determined by assaying the numbers of fat-producing cells at each time point in the 11-day period assayed. The person skilled in the art would appreciate that differentiation of test cells into adipocytes may continue albeit at below optimum even after the 11-day period assay, i.e., even after 21 days incubation of the test cells in adipogenic media.

Accordingly, incubation in low-serum medium (0-1% FBS) for about 5-9 days followed by detachment from the plates using a protease, is considered optimum for producing cells that are capable of differentiating into different cell types from fibroblasts. For example, differentiation of the cell product into other cell types is achieved by reseeding the cells described above into differentiation media for adipocytes, or as described herein e.g., Examples 14 to 17.

EXAMPLE 2

Preparation of Cells Having the Ability to Differentiate into Other Cell Types by Incubation in Low Serum Medium and Treatment with Protease and Optional Additional Incubation at High Cell Density Conditions To improve the yield of cells having the ability to differentiate into other cell types, the inventors sought to investigate the effect of high density cultures on plasticity. Specifically, the inventors sought to test whether or not the additional step of incubating cells at high density in a high density plating medium may produce equivalent or improved results as the combined action of low serum incubation for 5-9 days and incubation in the presence of protease or alternatively by agonism of the Akt/(PKB) and/or the NF-κB pathway using an agonist compound. Without being bound by any theory or mode of action, the inventors reasoned that culturing protease treated cells at high cell density in a high density plating medium before attachment of the cells to each other and/or to the culture vessel, further induces activation of the NF-κB pathway. The inventor reasoned that an advantage of using a high cell density following protease treatment to induce the NF-κB pathway, in concert with incubating cells in low-serum conditions for 5-9 days and incubation in the presence of a protease and/or inducing the Akt/(PKB) and/or the NF-κB pathway using an agonist compound, is the increase in proportion of cells achieving optimum plasticity, and therefore increase in proportion of progenitor cells produced the method of the invention as described herein.

In this set of experiments for producing cells having the ability to differentiate into different cell types, fresh human dermal fibroblasts derived from adult skin or from foreskin fibroblasts are cultured under low serum conditions essentially as described in Example 1. At the conclusion of the incubation period in low serum media, test cells are detached by the addition of 20 µl of detachment solution comprising 0.12% trypsin, 0.02% EDTA and 0.04% glucose (SAFC Biosciences, Cat #59430C) and incubated at 37° C. until cells lifted from the plates.

Optionally, test cells are recovered from culture and are diluted to about 100,000 cells in 100 µl in high density plating medium (Medium 199 comprising 170 nM insulin, 0.5 mM 3-isobutyl-1-methylxanthine, 0.2 mM indomethacin, 1 µM dexamethasone, and 15% rabbit serum).

Within about 4 to 6 hours after trypsinization, test cells are recovered from culture and seeded at concentrations of about 100,000 cells per well/plate or at about 3703.7 cells per $mm^2$ surface area of the well/plate before attachment of the cells to the plate/well directly in 400 µl high density plating medium (e.g., Medium 199 comprising 170 nM insulin, 0.5 mM 3-isobutyl-1-methylxanthine, 0.2 mM indomethacin, 1 µM dexamethasone, and 15% rabbit serum) for a time and under conditions sufficient for an optimum number of progenitor cells to be produced e.g., for up to about 24 hours or until adherence is achieved i.e., a shorter time than required for cells to become adherent and/or as determined by analysis of cell marker expression and/or by the ability of aliquots of cells to subsequently undergo differentiation.

As a negative control for the production of progenitor cells, trypsinized cells are seeded at a reduced density i.e., about 740.1 cells per $mm^2$ surface area, in high density plating medium (e.g., Medium 199 comprising 170 nM insulin, 0.5 mM 3-isobutyl-1-methylxanthine, 0.2 mM indomethacin, 1 µM dexamethasone, and 15% rabbit serum) and incubated as for samples seeded at high density e.g., for up to about 24 hours or until adherence is achieved i.e., a shorter time than required for cells to become adherent and/or as determined by analysis of cell marker expression and/or by the ability of aliquots of cells to subsequently undergo differentiation.

Differentiation into Adipocytes

For differentiation into adipocytes, cells are incubated in adipogenic medium (Medium 199 comprising 170 nM insulin, 0.5 mM 3-isobutyl-1-methylxanthine, 0.2 mM indomethacin, 1 µM dexamethasone, and 15% rabbit serum) and allowed to expand for about 10-21 days.

As a negative control for differentiation, trypsinized cells are seeded at high density in high density plating medium (e.g., DMEM and 10% FCS) and incubated as for test samples seeded at high density e.g., for up to about 24 hours or until adherent and/or as determined by analysis of cell marker expression and/or by the ability of aliquots of cells to subsequently undergo differentiation. The high density plating medium is then replaced with 400 µl DMEM-HG medium and cells are allowed to expand for about 10-21 days.

As positive control for differentiation, rat bone marrow stromal/stem cells (rBMSCs) are expanded in DMEM medium comprising L-Glutamine and 10% FCS, and allowed to attach and reach sub-confluence or confluence. These cells are then detached by incubation with trypsin as described above, and seeded at concentration of about 50,000 cells per well/plate or at about 1851.9 cells per mm² surface area of the well/plate in 400 µl DMEM-HG comprising 10% FCS for up to about 24 hours or until adherent. The medium is replaced from adherent culture with 400 µl adipogenic medium (Medium 199 comprising 170 nM insulin, 0.5 mM 3-isobutyl-1-methylxanthine, 0.2 mM indomethacin, 1 µM dexamethasone, and 15% rabbit serum) and cells are allowed to expand for about 10-21 days.

Medium is replaced every 3 days for both test cells and negative and positive control cells.

Assessment of Adipogenesis

After incubation for 12-21 days in adipogenic medium, differentiation potential of test cells compared to control cells at each day of incubation at high density post incubation with low-serum and trypsinization is measured by an assessment of adipogenisis as described above.

EXAMPLE 3

Preparation of Cells Having the Ability to Differentiate into Other Cell Types by Induction of the Akt/(PKB) Pathway: Method 1

The data in Example 1 suggested to the inventor that agonism of the Akt/(PKB) pathway and/or NF-κB pathway may produce equivalent or improved results as the combined action of low-serum incubation for 5-9 days and incubation in the presence of a protease such as trypsin to detach cells. Without being bound by any theory or mode of action, the inventor reasoned that the time required for low serum incubation to induce optimum plasticity of fibroblasts coincided with the time course for induction of the Akt/(PKB) pathway, and that the responses of cells to the combined low-serum and trypsinization conditions was likely to induce the Akt/(PKB) pathway. Accordingly, the inventor sought to test whether or not the effect of low-serum incubation for 5-9 days and incubation in the presence of a protease such as trypsin could be reproduced or improved upon by incubation in the presence of one or more agonists of the Akt/(PKB) pathway. An advantage of using an agonist to induce the Akt/(PKB) pathway, as opposed to incubating cells in low-serum condition followed by trypsinization, or in concert with such a process, is the shorter time period for achieving optimum plasticity. By reducing the time period for inducing the Akt/(PKB) pathway using an agonist compound, differentiated primary cells and cell lines that would normally enter a quiescent state or undergo apoptosis in low-serum media for 5-9 days can be used to produce cells capable of differentiating into different cell types.

In one example to show that Akt/(PKB) pathway induction confers or enhances plasticity of fibroblasts, primary human foreskin fibroblasts are incubated in the presence of human recombinant PDGF-BB for a time and under conditions sufficient to induce the Akt/(PKB) pathway.

Production of Cells Capable of Differentiating into Different Cell Types

Fresh human dermal fibroblasts that are derived from adult skin or from foreskin are purchased from PromoCell® (Banksia Scientific Company, QLD). Human dermal fibroblasts are plated in cell culture flasks, or plates, in growth medium (DMEM-HG; e.g., Lonza) supplemented with 10% FBS (fetal bovine serum), and incubated at 37° C. in a humidified atmosphere of 5% $CO_2$ in air until adherent. Once all cells are attached, the medium is replaced with medium 199 (e.g., Sigma) supplemented with 0-1% FBS (low-serum) for 24 hours to precondition the cells for PDGF-BB treatment. After 24 hours, the medium is replaced with low-serum or serum-free medium 199 comprising 10 to 100 ng/ml of human recombinant PDGF-BB (Invitrogen) for 5 to 15 min to activate the Akt/(PKB) pathway. Optionally, cells are maintained on low-serum medium for an additional 5-9 days.

Preferably, treated adherent cells are detached from plates by the addition of 20 µl of detachment solution comprising 0.12% Trypsin, 0.02% EDTA and 0.04% Glucose (SAFC Biosciences, Cat #59430C) and are incubated at 37° C. cells lifted from the plates. Treated cells are recovered from culture, then diluted to 200 µl with serum-free medium 199 (e.g., Sigma Cat #2154) (0% FBS) and maintained in serum-free medium until required for differentiation.

Differentiation into Other Cell Types

Re-differentiation of the treated fibroblasts into other cell types is achieved by reseeding the treated cells described above into differentiation media, preferably after trypsinization and before reattachment. Methods suitable for differentiation of these cells into adipocytes, cells of osteogenic lineage, chondrogenic lineage, haematopoietic cells or insulin secreting cells are known in the art and described herein e.g., Example 1 and Examples 15 to 18.

EXAMPLE 4

Preparation of Cells Having the Ability to Differentiate into Other Cell Types by Induction of the Akt/(PKB) Pathway: Method 2

In a further example to show that Akt/(PKB) pathway induction confers or enhances plasticity of fibroblasts, primary fibroblasts are incubated in the presence of TGF-β for a time and under conditions sufficient to induce the Akt/(PKB) pathway.

Production of Cells Capable of Differentiating into Different Cell Types

Fresh human dermal fibroblasts derived from adult skin or from foreskin are purchased from PromoCell® (Banksia Scientific Company, QLD). Human dermal fibroblasts are plated in cell culture flasks, or plates, in growth medium (DMEM-HG; e.g., Lonza) supplemented with 10% FBS (fetal bovine serum), and incubated at 37° C. in a humidified atmosphere of 5% $CO_2$ in air until adherent. Once all cells are attached, the medium is replaced with DMEM-HG (e.g., Lonza) supplemented with 0-1% FBS (low-serum) for 24 hours to precondition the cells for TGF-β treatment. After 24 hours, the medium is replaced with serum-free or low-serum medium 199 (M199) (e.g., Sigma) comprising 1 to 10 ng/ml of TGF-β (R&D systems) for at least 60 min to activate the Akt/(PKB) pathway. Optionally, cells are maintained on low-serum medium for an additional 5-9 days.

Preferably, treated adherent cells are detached from plates by the addition of 20 µl of detachment solution comprising 0.12% Trypsin, 0.02% EDTA and 0.04% Glucose (SAFC Biosciences, Cat #59430C) and are incubated at 37° C. until cells lifted from the plates. Treated cells are recovered from culture, then diluted to 200 µl with serum-free medium 199 (e.g., Sigma Cat #2154) (0% FBS) and maintained in serum-free medium until required for re-differentiation.
Differentiation into Other Cell Types Re-differentiation of the treated fibroblasts into other cell types is achieved by reseeding the treated cells described above into differentiation media, preferably after trypsinization and before reattachment. Methods suitable for differentiation of these cells into adipocytes, cells of osteogenic lineage, chondrogenic lineage, haematopoietic cells or insulin secreting cells are known in the art and described herein e.g., Example 1 and Examples 15 to 18.

EXAMPLE 5

Preparation of Cells Having the Ability to Differentiate into Other Cell Types by Induction of the Akt/(PKB) Pathway: Method 3

In a further example to show that Akt/(PKB) pathway induction confers or enhances plasticity of fibroblasts, primary fibroblasts are incubated in the presence of sodium pyruvate for a time and under conditions sufficient to induce the Akt/(PKB) pathway.
Production of Cells Capable of Differentiating into Different Cell Types Fresh human dermal fibroblasts derived from adult skin or from foreskin are purchased from PromoCell® (Banksia Scientific Company, QLD). Human dermal fibroblasts are plated in cell culture flasks, or plates, in growth medium (DMEM-HG without sodium pyruvate; for example Lonza Cat. #12-741) supplemented with 10% FBS (fetal bovine serum), and incubated at 37° C. in a humidified atmosphere of 5% $CO_2$ in air until adherent. Once all cells are attached, the medium is replaced with medium 199 (e.g., Sigma) without sodium pyruvate supplemented with 0-1% FBS (low-serum) for 24 hours to precondition the cells for sodium pyruvate treatment. After 24 hours, the medium is replaced with serum-free or low-serum medium 199 comprising 50 to 200 mg/L of cell culture grade sodium pyruvate (e.g., Lonza), and preferably, at 110 mg/L for at least 1 h to activate the Akt/(PKB) pathway. Optionally, cells are maintained on low-serum medium with sodium pyruvate for an additional 5-9 days.

Preferably, treated adherent cells are detached from plates by the addition of 20 µl of detachment solution comprising 0.12% Trypsin, 0.02% EDTA and 0.04% Glucose (SAFC Biosciences, Cat #59430C) and are incubated at 37° C. until cells lifted from the plates. Treated cells are recovered from culture, then diluted to 200 µl with serum-free medium 199 (e.g., Sigma Cat #2154) with sodium pyruvate (0% FBS) and maintained in serum-free medium until required for re-differentiation.
Differentiation into Other Cell Types Re-differentiation of the treated fibroblasts into other cell types is achieved by reseeding the treated cells described above into differentiation media, preferably after trypsinization and before reattachment. Methods suitable for differentiation of these cells into adipocytes, cells of osteogenic lineage, chondrogenic lineage, haematopoietic cells or insulin secreting cells are known in the art and described herein e.g., Example 1 and Examples 15 to 18.

EXAMPLE 6

Preparation of Cells Having the Ability to Differentiate into Other Cell Types by Induction of the Akt/(PKB) Pathway: Method 4

In a further example to show that Akt/(PKB) pathway induction confers or enhances plasticity of fibroblasts, mouse dermal primary fibroblasts are incubated in the presence of PDGF-BB for a time and under conditions sufficient to induce the Akt/(PKB) pathway.
Production of Cells Capable of Differentiating into Different Cell Types Mouse dermal fibroblast cells are prepared from 8- to 12-week-old C57BL/6 mice. Briefly, mice are anesthetized with pentobarbital (50 mg/kg body weight), and a full thickness of the back skin is cut out by scissors. The skin tissues are cut into small pieces and are implanted into plastic tissue culture dishes comprising DMEM-HG (e.g., Lonza) with 10% FBS. The fibroblast cultures are used after three to seven passages.

Adherent fibroblast cultures are incubated in medium 199 (e.g., Sigma) supplemented with 0-1% FBS (low-serum) for 48 hours to precondition the cells for PDGF-BB treatment. After 48 hours, the medium is replaced with serum-free medium 199, Sigma) or low-serum medium 199 comprising 10 to 100 ng/ml of human recombinant PDGF-BB (Invitrogen) for 15 to 60 min to activate the Akt/(PKB)/(PKB) pathway. Optionally, cells are maintained on low-serum medium for an additional 5-9 days.

Preferably, treated cells are detached from plates by the addition of 20 µl of detachment solution comprising 0.12% Trypsin, 0.02% EDTA and 0.04% Glucose (SAFC Biosciences, Cat #59430C) and are incubated at 37° C. until cells lifted from the plates. Treated cells are recovered from culture, then diluted to 200 µl with serum-free medium 199 (e.g., Sigma Cat #2154) (0% FBS) and maintained in serum-free medium until required for re-differentiation.
Differentiation into Other Cell Types Re-differentiation of the treated fibroblasts into other cell types is achieved by reseeding the treated cells described above into differentiation media, preferably after trypsinization and before reattachment. Methods suitable for differentiation of these cells into adipocytes, cells of osteogenic lineage, chondrogenic lineage, haematopoietic cells or insulin secreting cells are known in the art and described herein e.g., Example 1 and Examples 15 to 18.

EXAMPLE 7

Preparation of Cells Having Other Cell Types by Induction of the Akt/(PKB) Pathway: Method 5

In a further example to show that Akt/(PKB) pathway induction confers or enhances plasticity of cells generally, rat adrenal cells are incubated in the presence of Carbachol or NGF for a time and under conditions sufficient to induce the Akt/(PKB) pathway.
Production of Cells Capable of Differentiating into Different Cell Types PC12 cells are obtained from the American Type Culture Collection (CRL-1721, Rockville, Md.). PC12 cells are cultured in DMEM-HG supplemented with 5% (v/v) fetal calf serum and 10% (v/v) heat-inactivated horse serum, and grown at 37° C. in an environment of 7.5% $CO_2$ as described previously (Yu et al, *Neurosignals* 13: p 248 (2004).

Adherent PC12 cultures are incubated in medium 199 (e.g., Sigma) supplemented with 0-1% FBS (low-serum) for 24 hours to precondition the cells for Carbachol treatment. After 24 hours, the medium is replaced with serum-free medium 199 or low-serum DMEM comprising 200-1000 µM Carbachol (Calbiochem) or at least 50 ng/ml purified NGF (2.5S) (Alomone Labs Ltd) for 5 to 10 min to activate the Akt/(PKB) pathway. Optionally, cells are maintained on low-serum medium for an additional 5-9 days.

Preferably, treated adherent cells are detached from larger plates by the addition of 20 µl of detachment solution comprising 0.12% Trypsin, 0.02% EDTA and 0.04% Glucose (SAFC Biosciences, Cat #59430C) and are incubated at 37° C. until cells lifted from the plates. Treated cells are recovered from culture, then diluted to 200 µl with serum-free medium 199 (e.g., Sigma Cat #2154) (0% FBS) and maintained in serum-free medium until required for re-differentiation.

Differentiation into Other Cell Types

Re-differentiation of the treated adrenal cells into other cell types is achieved by reseeding the treated cells described above into differentiation media, preferably after trypsinization and before reattachment. Methods suitable for differentiation of these cells into adipocytes, cells of osteogenic lineage, chondrogenic lineage, haematopoietic cells or insulin secreting cells are known in the art and described herein e.g., Example 1 and Examples 15 to 18.

EXAMPLE 8

Preparation of Cells Having the Ability to Differentiate into Other Cell Types by Induction of the Akt/(PKB) Pathway: Method 6

In a further example to show that Akt/(PKB) pathway induction confers or enhances plasticity of cells generally, embryo fibroblasts are incubated in the presence of insulin growth factor-1 (IGF-1) for a time and under conditions sufficient to induce the Akt/(PKB) pathway.

Production of Cells Capable of Differentiating into Different Cell Types

Non-transformed rat embryo fibroblasts (Rat-1) are prepared and maintained as previously described (Peterson, et al., J. Biol. Chem. 271:31562-31571 (1996)).

Adherent Rat-1 cultures are incubated in DMEM-HG supplemented with 0-1% FBS (low-serum) for 12 hours to precondition the cells for IGF-1 treatment. After 12 hours, the medium is replaced with serum-free DMEM or low-serum DMEM comprising at least 250 ng/ml of insulin growth factor-1 (IGF-1; Sigma) for at least about 20 min to activate the Akt/(PKB) pathway. Optionally, cells are maintained on low-serum medium for an additional 5-9 days.

Preferably, treated adherent cells are detached from plates by the addition of 20 µl of detachment solution comprising 0.12% Trypsin, 0.02% EDTA and 0.04% Glucose (SAFC Biosciences, Cat #59430C) and are incubated at room temperature until cells lifted from the plates. Treated cells are recovered from culture, then diluted to 200 µl with serum-free medium 199 (e.g., Sigma Cat #2154) (0% FBS) and maintained in serum-free medium until required for re-differentiation.

Differentiation into Other Cell Types

Re-differentiation of the treated adrenal cells into other cell types is achieved by reseeding the treated cells described above into differentiation media, preferably after trypsinization and before reattachment. Methods suitable for differentiation of these cells into adipocytes, cells of osteogenic lineage, chondrogenic lineage, haematopoietic cells or insulin secreting cells are known in the art and described herein e.g., Example 1 and Examples 15 to 18.

EXAMPLE 9

Preparation of Cells Having the Ability to Differentiate into Other Cell Types by Induction of the NF-κB Pathway: Method 1

The data in example 1 also suggested to the inventor that agonism of the NF-κB pathway may produce equivalent or improved results as the combined action of low-serum incubation for 5-9 days and incubation in the presence of a protease such as trypsin to detach cells, and optional maintenance, culture or incubation at high cell density in high cell density plating medium. Without being bound by any theory or mode of action, the inventor reasoned that the time required for low serum incubation to induce optimum plasticity of fibroblasts coincided with the time course for induction of the NF-κB pathway, and that the responses of cells to the combined low-serum and trypsinization conditions was likely to induce the NF-κB pathway. Accordingly, the inventor sought to test whether or not the effect of low-serum incubation for 5-9 days and incubation in the presence of a protease such as trypsin could be reproduced or improved upon by incubation in the presence of one or more agonists of the NF-κB pathway. An advantage of using an agonist to induce the NF-κB pathway, in concert with or as opposed to incubating cells in low-serum condition followed by trypsinization, and optional maintenance, culture or incubation at high cell density in high cell density plating medium, is the shorter time period for achieving optimum plasticity. By reducing the time period for inducing the NF-κB pathway using an agonist, differentiated primary cells and cell lines that would normally enter a quiescent state or undergo apoptosis in low-serum media for 5-9 days can be used to produce cells capable of differentiating into different cell types.

In one example to show that NF-κB pathway induction confers or enhances plasticity of cells generally, primary human dermal fibroblasts are incubated in the presence of TNF-α for a time and under conditions sufficient to induce the NF-κB pathway.

Production of Cells Capable of Differentiating into Different Cell Types

Fresh human dermal fibroblasts derived from adult skin or from foreskin are purchased from PromoCell® (Banksia Scientific Company, QLD). Human dermal fibroblasts are plated in cell culture flasks, or plates, in growth medium (DMEM-HG) supplemented with 10% FBS (fetal bovine serum), and incubated at 37° C. in a humidified atmosphere of 5% $CO_2$ in air until adherent. Once all cells are attached, the medium is replaced with serum-free medium 199 (e.g., Sigma) or low-serum medium 199 (e.g., Sigma) comprising at least 20 ng/ml of TNF-α (Roche) for at least 60 min to activate the NF-κB pathway. Optionally, cells are maintained on low-serum medium for an additional 5-9 days.

Preferably, treated adherent cells are detached from plates by the addition of 20 µl of detachment solution comprising 0.12% Trypsin, 0.02% EDTA and 0.04% Glucose (SAFC Biosciences, Cat #59430C) and are incubated at 37° C. until cells lifted from the plates. Treated cells are recovered from culture, then diluted to 200 µl with serum-free medium 199 (e.g., Sigma Cat #2154) (0% FBS) and maintained in serum-free medium until required for re-differentiation. Optionally, for high density plating, treated cells are recovered from culture within about 4-6 hours after trypsinization, and are diluted to about 100,000 cells in 100 µl in a high density plating medium. Cells are then seeded directly in the high density plating medium at high cell density of about 100,000 cells per well (i.e., 100 µl per well) or at about 3703.7 cells per mm$^2$ surface area of the well before adherence of the cells to the plates and the cell are allowed to expand.

Differentiation into Other Cell Types

Re-differentiation of the treated adrenal cells into other cell types is achieved by reseeding the treated cells described above into differentiation media, preferably after trypsinization and before reattachment. Methods suitable for differentiation of these cells into adipocytes, cells of osteogenic lineage, chondrogenic lineage, haematopoietic cells or insulin secreting cells are known in the art and described herein e.g., Examples 1 and 2, and Examples 15 to 18.

EXAMPLE 10

Preparation of Cells Having the Ability to Differentiate into Other Cell Types by Induction of the NF-κB Pathway: Method 2

In a further example to show that NF-κB pathway induction confers or enhances plasticity of cells generally, primary human dermal fibroblasts are incubated in the presence of interleukin-1α for a time and under conditions sufficient to induce the NF-κB pathway.

Production of Cells Capable of Differentiating into Different Cell Types

Fresh human dermal fibroblasts derived from adult skin or from foreskin are purchased from PromoCell® (Banksia Scientific Company, QLD). Human dermal fibroblasts are plated in cell culture flasks, or plates, in growth medium (DMEM-HG) supplemented with 10% FBS (fetal bovine serum), and incubated at 37° C. in a humidified atmosphere of 5% CO$_2$ in air until adherent. Once all cells are attached, the medium is replaced with medium 199 (e.g., Sigma) supplemented with 0.25% FBS for 50 hours to precondition the cells for IL-1α treatment. After 50 hours, the cells are treated with recombinant human IL-1α at a concentration of least 0.27 ng/ml to activate the NF-κB pathway. Optionally, cells are maintained on low-serum medium for an additional 5-9 days.

Preferably, treated adherent cells are detached from plates by the addition of 20 µl of detachment solution comprising 0.12% Trypsin, 0.02% EDTA and 0.04% Glucose (SAFC Biosciences, Cat #59430C) and are incubated at 37° C. until cells lifted from the plates. Treated cells are recovered from culture, then diluted to 200 µl with serum-free medium 199 (e.g., Sigma Cat #2154) (0% FBS) and maintained in serum-free medium until required for re-differentiation. Optionally, for high density plating, treated cells are recovered from culture within about 4-6 hours after trypsinization, and are diluted to about 100,000 cells in 100 µl in high density plating medium. Cells are then seeded directly in the high density plating medium at high cell density of about 100,000 cells per well (i.e., 100 µl per well) or at about 3703.7 cells per mm$^2$ surface area of the well before adherence of the cells to the plates and the cell are allowed to expand.

Differentiation into Other Cell Types

Re-differentiation of the treated adrenal cells into other cell types is achieved by reseeding the treated cells described above into differentiation media, preferably after trypsinization and before reattachment. Methods suitable for differentiation of these cells into adipocytes, cells of osteogenic lineage, chondrogenic lineage, haematopoietic cells or insulin secreting cells are known in the art and described herein e.g., Examples 1 and 2 and Examples 15 to 18.

EXAMPLE 11

Preparation of Cells Having the Ability to Differentiate into Other Cell Types by Induction of the NF-κB Pathway: Method 3

In a further example to show that NF-κB pathway induction confers or enhances plasticity of fibroblasts, primary fibroblasts are incubated in the presence of sodium pyruvate for a time and under conditions sufficient to induce the NF-κB pathway.

Production of Cells Capable of Differentiating into Different Cell Types

Fresh human dermal fibroblasts derived from adult skin or from foreskin are purchased from PromoCell® (Banksia Scientific Company, QLD). Human dermal fibroblasts are plated in cell culture flasks, or plates, in growth medium (DMEM-HG without sodium pyruvate; for example Lonza Cat. #12-741) supplemented with 10% FBS (fetal bovine serum), and incubated at 37° C. in a humidified atmosphere of 5% CO$_2$ in air until adherent. Once all cells are attached, the medium is replaced with DMEM-HG without sodium pyruvate (e.g., Lonza) supplemented with 0-1% FBS (low-serum) for 24 hours to precondition the cells for sodium pyruvate treatment. After 24 hours, the medium is replaced with serum-free or low-serum medium 199 (e.g., Sigma) with sodium pyruvate comprising 50 to 200 mg/L of cell culture grade sodium pyruvate (e.g., Lonza), and preferably, at 110 mg/L for at least 1 h to activate the NF-κB pathway. Optionally, cells are maintained on low-serum medium with sodium pyruvate for an additional 5-9 days.

Preferably, treated adherent cells are detached from plates by the addition of 20 µl of detachment solution comprising 0.12% Trypsin, 0.02% EDTA and 0.04% Glucose (SAFC Biosciences, Cat #59430C) and are incubated at 37° C. until cells lifted from the plates. Treated cells are recovered from culture, then diluted to 200 µl with serum-free medium 199 (e.g., Sigma Cat #2154) with sodium pyruvate (e.g., Lonza Cat #12-604) (0% FBS) and maintained in serum-free medium until required for re-differentiation. Optionally, for high density plating, treated cells are recovered from culture within about 4-6 hours after trypsinization, and are diluted to about 100,000 cells in 100 µl in high density plating medium. Cells are then seeded directly in the high density plating medium at high cell density of about 100,000 cells per well (i.e., 100 µl per well) or at about 3703.7 cells per mm$^2$ surface area of the well before adherence of the cells to the plates and the cell are allowed to expand.

Differentiation into Other Cell Types

Re-differentiation of the treated fibroblasts into other cell types is achieved by reseeding the treated cells described above into differentiation media, preferably after trypsinization and before reattachment. Methods suitable for differentiation of these cells into adipocytes, cells of osteogenic lineage, chondrogenic lineage, haematopoietic cells or insulin secreting cells are known in the art and described herein e.g., Examples 1 and 2 Examples 15 to 18.

EXAMPLE 12

Preparation of Cells Having the Ability to Differentiate into Other Cell Types by Induction of the NF-κB Pathway: Method 4

In a further example to show that NF-κB pathway induction confers or enhances plasticity of cells generally, mouse embryo fibroblasts are incubated in the presence of L-alpha-Lysophosphatidic acid (C18:1, [cis]-9), LPA for a time and under conditions sufficient to induce the NF-κB pathway.

Production of Cells Capable of Differentiating into Different Cell Types

Swiss 3T3 mouse embryo fibroblasts are obtained from the American Type Culture Collection (CCL-92, Rockville, Md.) and are cultured at 37 C under a humidified atmosphere of 10% $CO_2$ in Dulbecco's modified Eagle's medium (DMEM) comprising 10% (v/v) fetal calf serum.

Adherent 3T3 fibroblast cultures are incubated in DMEM-HG supplemented with 1% FBS (low-serum) for 18 hours to precondition the cells for L-α-Lysophosphatidic acid (C18:1,[cis]-9), LPA treatment. After 18 hours, L-α-Lysophosphatidic acid (C18:1,[cis]-9), LPA (Calbiochem); prepared as a stock of 1 mg/ml in phosphate-buffered saline comprising 10 mg/ml essentially fatty acid-free bovine serum albumin (Sigma) is added to adherent cultures at 40-100 μM final concentration for about 40-120 min to activate the NF-κB pathway. As a control, TNF-α (Roche) is added to separate parallel cultures at a final concentration of 30 ng/ml for the same time period to activate the NF-κB pathway e.g., as described in Example 8. Optionally, cells are maintained on low-serum medium for an additional 5-9 days.

Preferably, treated adherent cells are detached from larger plates by the addition of 20 μl of detachment solution comprising 0.12% Trypsin, 0.02% EDTA and 0.04% Glucose (SAFC Biosciences, Cat #59430C) and are incubated at room temperature until cells lifted from the plates. Treated cells are recovered from culture, then diluted to 200 μl with serum-free medium 199 (e.g., Sigma Cat #2154) (0% FBS) and maintained in serum-free medium until required for re-differentiation. Optionally, for high density plating, treated cells are recovered from culture within about 4-6 hours after trypsinization, and are diluted to about 100,000 cells in 100 μl in high density plating medium. Cells are then seeded directly in the high density plating medium at high cell density of about 100,000 cells per well (i.e., 100 μl per well) or at about 3703.7 cells per $mm^2$ surface area of the well before adherence of the cells to the plates and the cell are allowed to expand.

Differentiation into Other Cell Types

Re-differentiation of the treated adrenal cells into other cell types is achieved by reseeding the treated cells described above into differentiation media, preferably after trypsinization and before reattachment. Methods suitable for differentiation of these cells into adipocytes, cells of osteogenic lineage, chondrogenic lineage, haematopoietic cells or insulin secreting cells are known in the art and described herein e.g., Examples 1 and 2 and Examples 15 to 18.

EXAMPLE 13

Preparation of Cells Having the Ability to Differentiate into Other Cell Types by Induction of the NF-κB Pathway: Method 5

In a further example to show that NF-κB pathway induction confers or enhances plasticity of cells generally, human myometrial microvascular endothelial cells (HUMEC) are incubated in the presence of Lipopolysaccharide (LPS) for a time and under conditions sufficient to induce the NF-κB pathway.

Production of Cells Capable of Differentiating into Different Cell Types

Human myometrial microvascular endothelial cells (HU-MEC) are obtained from Technoclone GmbH (Vienna, Austria) and are cultured at 37 C in endothelial growth medium according to the specifications supplied by Technoclone GmbH.

Adherent HUMEC cultures are then incubated in endothelial medium, preferably serum free or comprising low-serum concentration, and supplemented with 10-100 ng/ml of Lipopolysaccharide (LPS; Sigma) for at least 45 min to activate the NF-κB pathway. Optionally, cells are maintained on low-serum medium for an additional 5-9 days.

Preferably, treated adherent cells are detached from larger plates by the addition of 20 μl of detachment solution comprising 0.12% Trypsin, 0.02% EDTA and 0.04% Glucose (SAFC Biosciences, Cat #59430C) and are incubated at 37° C. until cells lifted from the plates. Treated cells are recovered from culture, then diluted to 200 μl with serum-free medium 199 (e.g., Sigma Cat #2154) (0% FBS) and maintained in serum-free medium until required for re-differentiation. Optionally, for high density plating, treated cells are recovered from culture within about 4-6 hours after trypsinization, and are diluted to about 100,000 cells in 100 μl in high density plating medium. Cells are then seeded directly in the high density plating medium at high cell density of about 100,000 cells per well (i.e., 100 μl per well) or at about 3703.7 cells per $mm^2$ surface area of the well before adherence of the cells to the plates and the cell are allowed to expand.

Differentiation into Other Cell Types

Re-differentiation of the treated adrenal cells into other cell types is achieved by reseeding the treated cells described above into differentiation media, preferably after trypsinization and before reattachment. Methods suitable for differentiation of these cells into adipocytes, cells of osteogenic lineage, chondrogenic lineage, haematopoietic cells or insulin secreting cells are known in the art and described herein e.g., Examples 1 and 2 and Examples 15 to 18.

EXAMPLE 14

Preparation of Cells Having the Ability to Differentiate into Other Cell Types by Induction of the NF-κB Pathway: Method 6

In a further example to show that NF-κB pathway induction confers or enhances plasticity of cells generally, synovial fibroblasts are incubated in the presence of Lipopolysaccharide (LPS) for a time and under conditions sufficient to induce the NF-κB pathway.

Production of Cells Capable of Differentiating into Different Cell Types

Primary cultures of synovial fibroblasts are obtained and maintained in culture as described previously (Brinckerhoff, and Mitchell, Journal of Cellular Physiology, 136 (1):72-80 (2005)).

Adherent synovial fibroblast cultures are then incubated in growth medium, preferably serum free or comprising low-serum concentration, and supplemented with 10-100 ng/ml of Lipopolysaccharide (LPS; Sigma) for at least 45 min to activate the NF-κB pathway. Optionally, cells are maintained on low-serum medium for an additional 5-9 days.

Preferably, treated adherent cells are detached from larger plates by the addition of 20 μl of detachment solution comprising 0.12% Trypsin, 0.02% EDTA and 0.04% Glucose (SAFC Biosciences, Cat #59430C) and are incubated at 37° C. until cells lifted from the plates. Treated cells are recovered from culture, then diluted to 200 μl with serum-free medium 199 (e.g., Sigma Cat #2154) (0% FBS) and maintained in serum-free medium until required for re-differentiation. Optionally, for high density plating, treated cells are recovered from culture within about 4-6 hours after trypsinization, and are diluted to about 100,000 cells in 100 μl in high density plating medium. Cells are then seeded directly in the high density plating medium at high cell density of about 100,000 cells per well (i.e., 100 μl per well) or at about 3703.7 cells per mm$^2$ surface area of the well before adherence of the cells to the plates and the cell are allowed to expand.

Differentiation into Other Cell Types

Re-differentiation of the treated adrenal cells into other cell types is achieved by reseeding the treated cells described above into differentiation media, preferably after trypsinization and before reattachment. Methods suitable for differentiation of these cells into adipocytes, cells of osteogenic lineage, chondrogenic lineage, haematopoietic cells or insulin secreting cells are known in the art and described herein e.g., Examples 1 and 2 and Examples 15 to 18.

EXAMPLE 15

Differentiation of Cells into Cells of Osteogenic Lineage

This example describes methods for producing cells of osteogenic lineage from the cell product of any one of Examples 1 through 14 that is capable of being differentiated into a different cell type. This example also describes methods for testing that osteogenic cells are produced.

Differentiation Conditions

Cells capable of producing other cell types are prepared as in any one of Examples 1 to 14 and counted.

To produce cells of osteogenic lineage from such cells, the cells are incubated in complete osteogenic media (+DEX: DMEM-low glucose comprising 10% FBS, 20 μg/ml ascorbic acid phosphate-magnesium salt, 1.5 mg/ml beta glycerophosphate and 40 ng/ml dexamethasone) for differentiation to the osteogenic lineage, or in incomplete osteogenic media (–DEX: DMEM-low glucose comprising 10% FBS, 20 ug/ml ascorbic acid phosphate-magnesium salt, 1.5 mg/ml beta glycerophosphate), as a control. The cells are then plated in their respective media onto 96-well plates at about 20,000 cells per well or about 740.74 cells per mm$^2$ surface area of the well for alkaline phosphatase assays (ALP) or at 50,000 cells per well or about 1851.85 cells per mm$^2$ surface area of the well for mineral deposition assays as described below. Alternatively, the cells are plated in their respective differentiation media onto 96-well plates at about 100,000 cells per well or about 3703.7 cells per mm$^2$ surface area of the well where trypsinization is combined with high density plating e.g., as in Examples 2, and 9-14 Complete or incomplete osteogenic media is replaced every 3 days.

Assessment of Osteogenesis Using an Alkaline Phosphatase (ALP) Assay

After incubation for 12-21 days in either complete or incomplete osteogenic media as described above, alkaline phosphatase is assessed. The media is removed from cells; cells are washed in phosphate buffered saline and lysed with 40 μl of Passive Lysis Buffer (Promega). The lysate is sonicated. After sonication, the lysate is split into two equal samples of 20 μL each. One sample is placed into a separate 48 well plate, Add 180 uL of Hoescht 33258 in buffer (5 μg/mL in 2M NaCl or 20×SSC) (i.e 1:9 ratio of PLB to Hoescht) is added, and the sample is read at Excitation 350 nm/Emission 460 on Molecular Probes fluorescent scanner. p-Nitrophenyl phosphate (pNPP) 75 μL is added to the remaining sample and incubated for 30 minutes at 37° C. One hundred (100) μl of 2M NaOH is subsequently added which will turn into yellow p-Nitrophenylene anion –pNP. An aliquot of 100 μl is transferred to a 96 well plate for plate reading. The absorbance of pNP (yellow) is read on an optical plate reader at 405 nm. A comparison of +Dex to –Dex controls of Absorbance/ng DNA using a PNPP standard curve is made.

Assessment of Mineral Deposition

After incubation for 21 days in either complete or incomplete osteogenic media as described above, mineral deposition is assessed. To test for mineral deposition, cells are stained with Von Kossa. A comparison of staining intensity is performed on +Dex differentiated cells to –Dex treated controls.

EXAMPLE 16

Differentiation of Cells into Cells of Chondrogenic Lineage

This example describes methods for producing cells of chondrogenic lineage from the cell product of any one of Examples 1 through 14 that is capable of being differentiated into a different cell type. This example also described methods for testing that chondrogenic cells are produced.

Differentiation Conditions

Cells capable of producing other cell types are prepared as in any one of Examples 1 to 14 and counted.

To produce cells of chondrogenic lineage from such cells, the cells incubated in chondrogenic media (DMEM-HG comprising ITS+supplement at a 1 fold concentration (final concentrations of 6.25 μg/ml bovine insulin; 6.25 μg/ml transferrin; 6.25 μg/ml selenous acid; 5.33 μg/ml linoleic acid; 1.25 mg/ml BSA) 50 μg/ml ascorbic acid-2-phosphate, 40 μg/ml L-proline, 100 μg/ml pyruvate, 100 nM dexamethasone, 10 ng/ml TGF-β, and 500 ng/ml BMP-2) for differentiation to the chondrogenic lineage; or in DMEM-HG comprising 1.25 mg/ml BSA, as a control. The cells are then plated in their respective media onto 96-well plates at about 20,000-50,000 cells per well or at about 740.74-1851.85 cells per mm$^2$ surface area of the well. Alternatively, the cells are plated in their respective differentiation media onto 96-well plates at about 100,000 cells per well or at about 3703.7 cells per mm$^2$ surface area of the well where trypsinization is combined with high density plating e.g., as in Examples 2 and 9-14. Chondrogenic media or control media is replaced every 3 days.

Assessment of Chondrogenesis

After incubation for 12-21 days in either chondrogenic media or control media as described above, cells are assessed by observation for the appearance of chondrocyte morphology. Analysis of the accumulation of sulfated glycosaminoglycans (GAG) is carried out by measuring the amount of 1,9-dimethylmethylene blue-reactive material in extracts of cells treated with chondrogenic media and compared with extracts of control cells. The 1,9-dimethylmethylene blue assay is performed essentially as described in Sabiston et al, Analytical Biochemistry 149: 543-548 (1985).

EXAMPLE 17

Differentiation of Cells into Haematopoietic Cells

This example describes methods for producing haematopoietic cells from the cell product of any one of Examples 1 through 14 that is capable of being differentiated into a different cell type. This example also described methods for testing that haematopoietic cells are produced.
Differentiation Conditions Cells capable of producing other cell types are prepared as in any one of Examples 1 to 14 and counted.

To produce haematopoietic cells from such cells, the cells are mixed with DMEM supplemented with Granulocyte macrophage colony-stimulating factor (GM-CSF; 50 ng/ml) and stem cell factor (SCF; 50 ng/ml), plated onto 35-mm tissue culture dishes and are incubated at 37° C. in a humidified atmosphere of 5% $CO_2$ in air for 2 days. The cells are harvested and analyzed for cells expressing the hematopoietic marker CD45 by flow cytometry.

To detect the presence of the cell surface CD45 antigen, cells are incubated for 30 min. at 37° C. with anti-CD45 antibodies (Becton Dickinson), washed in PBS and analysed by flow cytometry. Flow cytometric analysis is performed using a FACSCalibur flow cytometer and the CellQuest software program (Becton Dickinson Immunocytometry Systems, San Jose, Calif.). Data analysis is performed using CellQuest and the Modfit LT V2.0 software program (Verity Software House, Topsham, Me.).

EXAMPLE 18

Differentiation of Cells into Insulin-Secreting Cells

This example describes methods for producing insulin-secreting cells from the cell product of any one of Examples 1 through 14 that is capable of being differentiated into a different cell type. This example also described methods for testing that insulin-secreting cells are produced.
Differentiation Conditions Cells capable of producing other cell types are prepared as in any one of Examples 1 to 14, and counted.

To produce insulin-secreting cells from such cells, the cells are plated into serum free medium to enrich for nestin-positive cells (see Lumelsky et al., Science, 292: 1389, 2001). The nestin-positive cells are then sub-subcultured and expanded for 6 to 7 days in serum-free N2 media supplemented with 1 μg/ml laminin, 10 ng/ml bFGF, 500 ng/ml N-terminal fragment of murine or human SHH (sonic hedge hog) 100 ng/ml FGF8 and B27 media supplement, as described in Lee et al. Nature Biotechnology, 18: 675 (2000) and Lumelsky (supra), which are herein incorporated by reference. After the nestin-positive cells are expanded, the growth factors (FGF, SHH) are removed from the media and nicotinamide is added to the media at a final concentration of 10 mM, to promote the cessation of cell proliferation and induce the differentiation of insulin-secreting cells. After approximately 6 days of growth factor starvation, aggregates of insulin-secreting cells are formed (islet-like cell clusters), which are autologous to the individual from whom they are derived.

EXAMPLE 19

Multipotency of Cells Produced in Accordance with the Invention

Retinoic Acid-Induced Differentiation of the Cells

Cells are tested for an ability to regenerate their telomeres, as determined by expression of telomerase. The expression of relatively high levels of telomerase in a cell culture is indicative of a stem cell-like phenotype. Furthermore, retinoic acid (RA)-induced differentiated cells down-regulate the expression of telomerase and express genes indicative of differentiating cells of various lineages. For example, Schuldiner et al., PNAS 97:11307 (2000) demonstrated the increased expression of tissue specific lineage markers, e.g., brain-specific neurofilament (ectodermal), heart-specific cardiac actin (mesodermal) and liver-specific α1-antitrypsin (endodermal), in cultures of human embryonic stem cells treated with RA.

Cells prepared as described in any one of Examples 1 to 14 are cultured in the presence of approximately 1-2 μM RA (Sigma, St. Louis) for 5 to 10 days, preferably in low-serum medium and/or the presence of one or more agonists of the Akt/(PKB) pathway and/or NF-κB pathway to maintain their plasticity.
RNA Extraction and RT-PCR To monitor the differential expression of various genes in the cells, reverse transcription-polymerase chain reaction (RT-PCR) is performed. RNA is extracted from untreated cells and cells treated with RA, e.g., using Perfect RNA™ Eukaryotic Kit (Eppendorf A G, Hamburg, D E), essentially according to the manufacturer's instructions. The extracted RNA is dissolved in RNase-free water e.g., provided in the Perfect RNA™ Eukaryotic Kit.

RT-PCR is performed using the QIAGEN® OneStep RT-PCR Kit (Qiagen Inc., Valencia, Calif.) according to the manufacturer's instructions. PCR amplification is preformed using the following protocol: 94° C. for 1 min., 55° C. for 1 min., 72° C. for 1 min., for 45 cycles.

The oligonucleotide primers set out below are used to detect the following mRNAs: human telomerase ("TRT"), neurofilament heavy chain ("NF"), alpha-antitrypsin ("αAT") and cardiac actin ("cACT"). To control for the quality of the extracted RNA and to serve as an internal quantification marker, human glyceraldehyde 3-phosphate dehydrogenase ("GAPDH") oligonucleotide primers are included in the RT-PCR reaction.

| RT-PCR primer sets: | | |
|---|---|---|
| GAPDH | 5'-GGGGAGCCAAAAGGGTCATCATCT-3'; | SEQ ID NO: 1 |
|  | 5'-GACGCCTGCTTCACCACCTTCTTG-3' | SEQ ID NO: 2 |
| TRT | 5'-CGGAGGTCATCGCCAGCATCATCA-3-' | SEQ ID NO: 3 |
|  | 5'-GTCCCGCCGAATCCCCGCAAACAG-3' | SEQ ID NO: 4 |
| NF | 5'-TGAACACAGACGCTATGCGCTCAG-3' | SEQ ID NO: 5 |
|  | 5'-CACCTTTATGTGAGTGGACACAGAG-3' | SEQ ID NO: 6 |
| αAT | 5'-AGACCCTTTGAAGTCAAGGACACCG-3' | SEQ ID NO: 7 |
|  | 5'-CCATTGCTGAAGACCTTAGTGATGC-3' | SEQ ID NO: 8 |
| cACT | 5'-TCTATGAGGGCTAGCCTTTG-3' | SEQ ID NO: 9 |
|  | 5'-CCTGACTGGAAGGTAGATGG-3' | SEQ ID NO: 10 |

The RT-PCR products are electrophoresed on 2% (w/v) agarose gels stained with ethidium bromide. The intensities of the DNA product bands are quantified e.g., using PHO-RETIX™ TotalLab densitometry software package developed by Nonlinear USA (Durham, N.C.). To determine the approximate relative percent change in the expression of TRT, NF, αAT and cACT in each of the experimental groups relative to the untreated fibroblasts the following equation is applied (Eq. 1):

$$x = ([a'/b')/(a/b)] - 1)100\%$$  Eq. 1 wherein x is the relative percent change in expression of the gene of interest; b is the intensity of the GAPDH band in untreated fibroblasts; b' is the intensity of the GAPDH band obtained from the experimental cells; a is the intensity of the gene-of-interest band obtained from the untreated fibroblasts; and a' is the intensity of the gene-of-interest band obtained from the experimental cells.

Cells that are ectodermal-like, or mesodermal-like or endodermal-like can be differentiated into specialized tissues normally derived from each embryonic layer and subsequently used for treatment and/or therapy of disease.

EXAMPLE 20

Therapy Using Differentiated Cells Produced in Accordance with the Invention This example describes therapeutic applications of progenitor cells produced from differentiated cells in accordance with the inventive method.

Diabetes

To treat human patients suffering from diabetes, progenitor cells are produced from differentiated cells and then differentiated into insulin-secreting cells as described in Example 18. Preferably, the differentiated cells used as starting material in this process were derived from the same patient or a matched patient to minimize or eliminate the risk of graft rejection. The insulin-secreting cells are grafted subcutaneously into a subject suffering from diabetes, wherein the cells are either encapsulated in a polymer matrix or non-encapsulated and comprising a suitable isotonic buffer, or surgically infused into the patient's pancreas. A therapeutic amount of insulin-secreting cells are implanted in the patient subcutaneously. The skilled practitioner may determine a therapeutic amount based upon the age, weight and general health of the patient and the amount of insulin secreted by said insulin-secreting cells in response to glucose administration. Blood glucose levels of the patient are monitored on a regular basis and the amount of implanted cells are adjusted accordingly.

Osteoarthritis

To treat human patients suffering from degenerative osteoarthritis, progenitor cells are produced from differentiated cells and then differentiated into chondrocytes as described in Example 17. Preferably, the differentiated cells used as starting material in this process were derived from the same patient or a matched patient to minimize or eliminate the risk of graft rejection. Cells of chondrocyte lineage are grafted into the diseased joints of a patient by implantation with a needle, or by orthoscopic surgical methods, wherein the cells are either encapsulated in a polymer matrix or non-encapsulated and comprising a suitable isotonic buffer. Again, a therapeutic amount of chondrocytes are implanted in the patient's degenerated joints. The skilled practitioner may determine a therapeutic amount based upon the age, weight and general health of the patient and the disease progression in the patient.

---

I claim:

1. A method for producing an adipocyte, said method comprising
    incubating a fibroblast cell in a low-serum medium comprising a low serum concentration and without supplementation of any factors normally present in serum, and
    detaching the fibroblast cell,
    incubating the detached fibroblast for a time and under conditions sufficient to produce an adipocyte.

2. The method according to claim 1, wherein the low-serum medium does not exceed about 3% (v/v) total serum concentration.

3. The method according to claim 1, comprising incubating the fibroblast cell in the low-serum medium for at least about 2 days and not exceeding about 10 days.

4. The method according to claim 1, comprising incubating the fibroblast cell for a period of time sufficient to induce and/or increase expression of one or more gene products that delay or inhibit or repress cell cycle progression.

5. The method according to claim 1, comprising detaching the fibroblast cell by incubating the fibroblast cell in a medium comprising a protease and/or incubating the fibroblast cell expressing one or more protease activated receptors (PARs) with one or more PAR ligands.

6. The method according to claim 1, comprising detaching the fibroblast cell by incubating the fibroblast cell in a medium comprising EDTA, wherein said medium is substantially $Ca^{2+}$-free and substantially $Mg^+$-free so as to not interfere with detachment.

7. The method according to claim 1, comprising detaching the fibroblast cell by incubating the fibroblast cell in a medium comprising a salt of citric acid.

8. The method according to claim 1, comprising incubating the fibroblast cell in a low-serum medium after detaching the fibroblast cell.

9. The method according to claim 1, wherein said method further comprises incubating the fibroblast cell in media comprising an agonist or partial agonist of the Akt/(PKB) pathway.

10. The method according to claim 1, wherein said method further comprises incubating the fibroblast cell in media comprising an agonist or partial agonist of the NF-kβ pathway.

11. The method according to claim 1, wherein said method further comprises incubating or maintaining or culturing the fibroblast cell in high cell-density conditions.

12. The method according to claim 1, further comprising isolating the adipocyte.

13. The method according to claim 1, further comprising storing the adipocyte.

* * * * *

SEQUENCE LISTING

```
<160> NUMBER OF SEQ ID NOS: 10

<210> SEQ ID NO 1
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 1
ggggagccaa aagggtcatc atct                                            24

<210> SEQ ID NO 2
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 2
gacgcctgct tcaccacctt cttg                                            24

<210> SEQ ID NO 3
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 3
cggaggtcat cgccagcatc atca                                            24
```

```
<210> SEQ ID NO 4
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 4
gtcccgccga atccccgcaa acag                                           24

<210> SEQ ID NO 5
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 5
tgaacacaga cgctatgcgc tcag                                           24

<210> SEQ ID NO 6
<211> LENGTH: 25
<212> TYPE: DNA
<213> ORGANISM: Artificial sequence
<220> FEATURE:
<223> OTHER INFORMATION: Synthetic nucleic acid

<400> SEQUENCE: 6
cacctttatg tgagtggaca cagag                                          25

<210> SEQ ID NO 7
<211> LENGTH: 25
<212> TYPE: DNA
<213> ORGANISM: Artificial sequence
<220> FEATURE:
<223> OTHER INFORMATION: Synthetic nucleic acid

<400> SEQUENCE: 7
agaccctttg aagtcaagga caccg                                          25

<210> SEQ ID NO 8
<211> LENGTH: 25
<212> TYPE: DNA
<213> ORGANISM: Artificial sequence
<220> FEATURE:
<223> OTHER INFORMATION: Synthetic nucleic acid

<400> SEQUENCE: 8
ccattgctga agaccttagt gatgc                                          25

<210> SEQ ID NO 9
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 9
tctatgaggg ctagcctttg                                                20

<210> SEQ ID NO 10
<211> LENGTH: 20
<212> TYPE: DNA
<213> ORGANISM: Artificial sequence
```

```
<220> FEATURE:
<223> OTHER INFORMATION: Synthetic nucleic acid

<400> SEQUENCE: 10
cctgactgga aggtagatgg                                              20
```